US010501528B2

(12) United States Patent
Saelens et al.

(10) Patent No.: US 10,501,528 B2
(45) Date of Patent: Dec. 10, 2019

(54) IMMUNOGLOBULIN SINGLE VARIABLE DOMAIN ANTIBODY AGAINST RSV PREFUSION F PROTEIN

(71) Applicants: VIB VZW, Ghent (BE); UNIVERSITEIT GENT, Ghent (BE); THE UNITED STATES OF AMERICA, AS REPRESENTED BY THE SECRETARY, DEPARTMENT OF HEALTH AND HUMAN SERVICES, Bethesda, MD (US); TRUSTEES OF DARTMOUTH COLLEGE, Hanover, NH (US)

(72) Inventors: Xavier Saelens, Ypres (BE); Bert Schepens, Drongen (BE); Iebe Rossey, Gentbrugge (BE); Barney Graham, Rockville, MD (US); Jason McLellan, Norwich, VT (US); Morgan Gilman, White River Junction, VT (US)

(73) Assignees: V18 VZW (BE); UNIVERSITEIT GENT (BE); THE UNITED STATES OF AMERICA, AS REPRESENTED BY THE SECRETARY OF HEALTH AND HUMAN SERVICES, Bethesda, MD (US); TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/736,663

(22) PCT Filed: Jun. 20, 2016

(86) PCT No.: PCT/EP2016/064218
§ 371 (c)(1),
(2) Date: Dec. 14, 2017

(87) PCT Pub. No.: WO2016/203052
PCT Pub. Date: Dec. 22, 2016

(65) Prior Publication Data

US 2018/0179266 A1 Jun. 28, 2018

Related U.S. Application Data

(60) Provisional application No. 62/181,522, filed on Jun. 18, 2015.

(30) Foreign Application Priority Data

Jul. 28, 2015 (EP) .................................... 15178653
Oct. 28, 2015 (EP) .................................... 15191868

(51) Int. Cl.

| | |
|---|---|
| ***C07K 16/10*** | (2006.01) |
| ***A61P 31/14*** | (2006.01) |
| ***A61K 39/12*** | (2006.01) |
| *A61K 39/00* | (2006.01) |

(52) U.S. Cl.
CPC .......... *C07K 16/1027* (2013.01); *A61K 39/12* (2013.01); *A61P 31/14* (2018.01); *A61K 2039/505* (2013.01); *A61K 2039/55561* (2013.01); *C07K 2317/22* (2013.01); *C07K 2317/565* (2013.01); *C07K 2317/569* (2013.01); *C07K 2317/76* (2013.01); *C12N 2760/18534* (2013.01)

(58) Field of Classification Search
None
See application file for complete search history.

(56) References Cited

U.S. PATENT DOCUMENTS

2012/0070446 A1 3/2012 Beaumont et al.

FOREIGN PATENT DOCUMENTS

| | | | |
|---|---|---|---|
| WO | 2008/147196 | A2 | 12/2008 |
| WO | 2009/079796 | A1 | 7/2009 |
| WO | 2009/147248 | A2 | 12/2009 |
| WO | 2010/139808 | A2 | 12/2010 |
| WO | 2011/064382 | A1 | 6/2011 |

OTHER PUBLICATIONS

Rudikoff et al., PNAS USA, 1982, 79:1979-1983. (Year: 1982).*
Neuzil, K.M., Clinical and Vaccine Immunology, 2016, 23:186-188. (Year: 2016).*
Corti et al. (Aug. 18, 2013) "Cross-neutralization of four paramyxoviruses by a human monoclonal antibody," Nature. 501(7467):439-443.
Gilman et al. (Jul. 10, 2015) "Characterization of a prefusion-specific antibody that recognizes a quaternary, cleavage-dependent epitope on the RSV fusion glycoprotein," PLoS Pathog. 11:1-17.
Hultberg et al. (2011) "Llama-derived single domain antibodies to build multivalent, superpotent and broadened neutralizing anti-viral molecules," PLoS One. 6:e17665. pp. 1-12.

(Continued)

*Primary Examiner* — Stacy B Chen

(74) *Attorney, Agent, or Firm* — Lathrop Gage LLP; James H. Velema, Esq.

(57) ABSTRACT

The present invention relates to immunoglobulin single variable domains (ISVDs) that are directed against respiratory syncytial virus (RSV). More specifically, it relates to ISVDs that bind to the prefusion form of the fusion (F) protein of RSV. The invention relates further to the use of these ISVDs for prevention and/or treatment of RSV infections, and to pharmaceutical compositions comprising these ISVDs.

12 Claims, 17 Drawing Sheets

Specification includes a Sequence Listing.

(56) References Cited

OTHER PUBLICATIONS

Lin-Cereghino et al. (2005) "Condensed protocol for competent cell preparation and transformation of the methylotrophic yeast Pichia pastoris," Biotechniques. 38:44,46,48.
Magro et al. (2012) "Neutralizing antibodies against the preactive form of respiratory syncytial virus fusion protein offer unique possibilities for clinical intervention," Proc. Natl. Acad. Sci. USA. 109(8):3089-3094.
McLellan et al. (2011) "Structure of respiratory syncytial virus fusion glycoprotein in the postfusion conformation reveals preservation of neutralizing epitopes," J. Virol. 85:7788-7796.
McLellan et al. (Apr. 25, 2013) "Structure of RSV fusion glycoprotein trimer bound to a prefusion-specific neutralizing antibody," Science. 340:1113-1117.
McLellan et al. (Nov. 1, 2013) "Structure-based design of a fusion glycoprotein vaccine for respiratory syncytial virus," Science. 342:592-598.
Schepens et al. (2011) "Nanobodies® specific for respiratory syncytial virus fusion protein protect against infection by inhibition of fusion," J. Infect Dis. 11:1692-1701.
Schoonooghe et al. (2009) "Efficient production of human bivalent and trivalent anti-MUC1 Fab-scFv antibodies in Pichia pastoris," BMC Biotechnol. 9:70.
Spits et al. (Feb. 2013) "Innate lymphoid cells—a proposal for uniform nomenclature," Nat. Rev. Immunol. 13 (2):145-149.
Swanson et al. (Jul. 30, 2014) "A Monomeric Uncleaved Respiratory Syncytial Virus F Antigen Retains Prefusion-Specific Neutralizing Epitopes," J. Virol. 88(2):11802-11810.
Tan et al. (May 22, 2013) "The comparative genomics of human respiratory syncytial virus subgroups A and B: genetic variability and molecular evolutionary dynamics," J Virol. 87:8213-8226.
International Search Report with Written Opinion corresponding to International Patent Application No. PCT/EP2016/064218, dated Oct. 6, 2016.

* cited by examiner

Figure 1
A
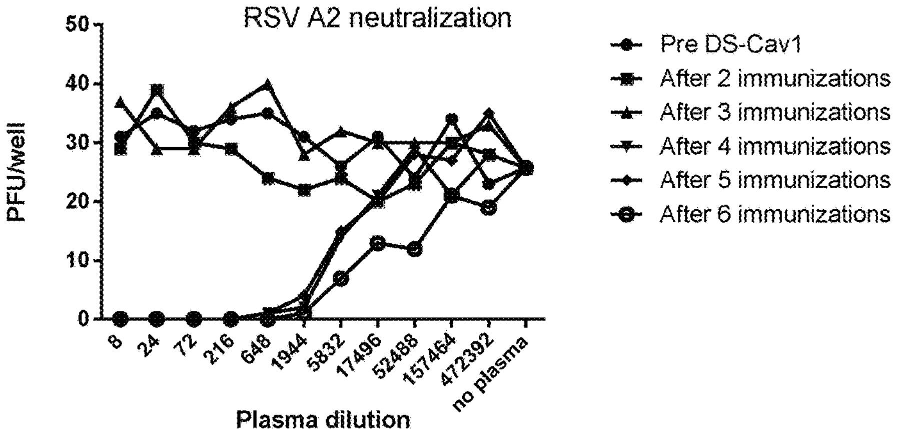
B
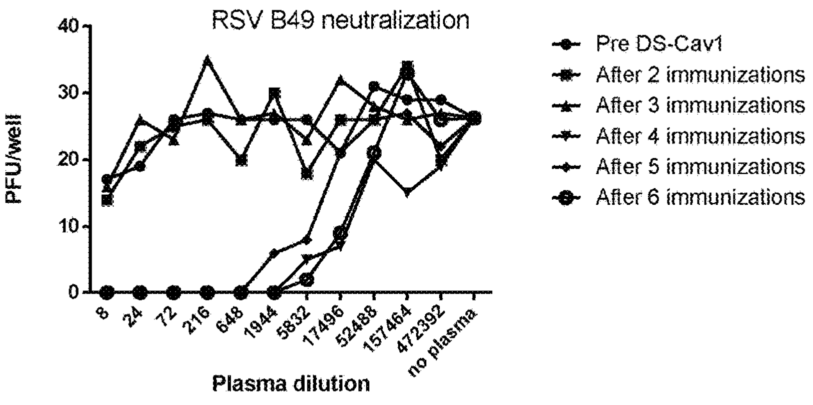

A

B

A

Figure 4 continued
B
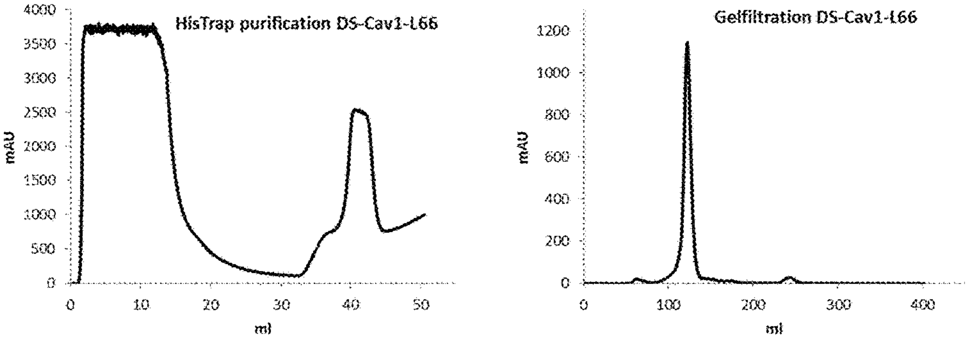
C
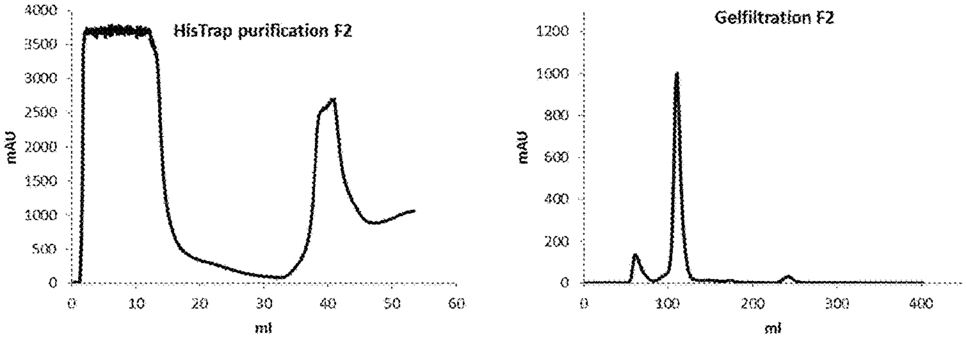
D
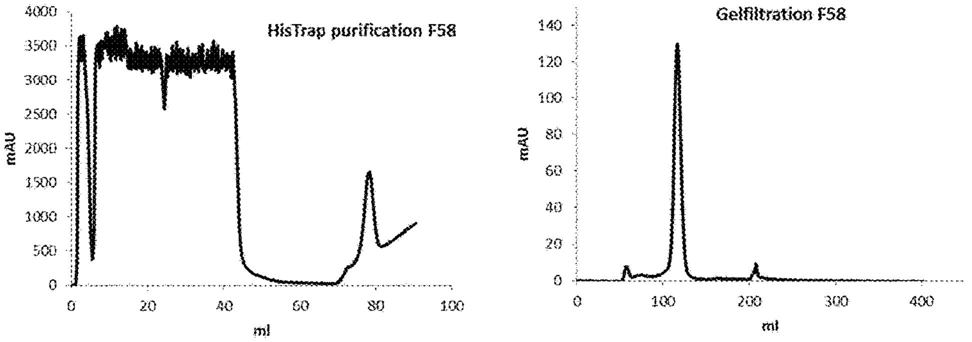

DS-Cav1-4

CAGGTGCAGCTGCAGGAGTCTGGGGGAGGCTTGGTGCAGCCTGGGGGGTCTCTGAGACTCTCCTGT
GCAGCCTCTGGATTCACTTTGGATTATTATTACATAGGCTGGTTCCGCCAGGCCCCAGGGAAGGAGCG
CGAGGCAGTCTCATGTATTAGTGGTAGTAGTGGTAGCACATACTATCCAGACTCCGTGAAGGGCCGAT
TCACCATCTCCAGAGACAATGCCAAGAACACGGTGTATCTGCAAATGAACAGCCTGAAACCTGAGGAC
ACGGCCGTTTATTACTGTGCGACAATTCGTAGTAGTAGCTGGGGGGGTTGCGTGCACTACGGCATGG
ACTACTGGGGCAAAGGGACCCAGGTCACCGTCTCCAGCCACCACCATCACCATCACTAG

B

DS-Cav1-L66

CAGGTGCAGCTGCAGGAGTCTGGGGGAGGCTTGGTGCAGCCTGGGGGGTCTCTGAGACTCTCCTGT
GCAGCCTCTGGATTCACTTTGGATTATTATTACATAGGCTGGTTCCGCCAGGCCCCAGGGAAGGAGCG
CGAGGGGGTCTCATGTATTAGTAGTAGTCATGGTAGCACATACTATGCAGACTCCGTGAAGGGCCGAT
TCACCATCTCCAGAGACAATGCCAAGAACACGGTGTATCTGCAGATGAACAGCCTGAAACCTGAGGAC
ACGGCCGTTTATTACTGTGCGACAGTAGCTGTAGCACATTTCCGGGGTTGCGGAGTCGACGGCATGG
ACTACTGGGGCAAAGGGACCCAGGTCACCGTCTCCAGCCACCACCATCACCATCACTAG

C

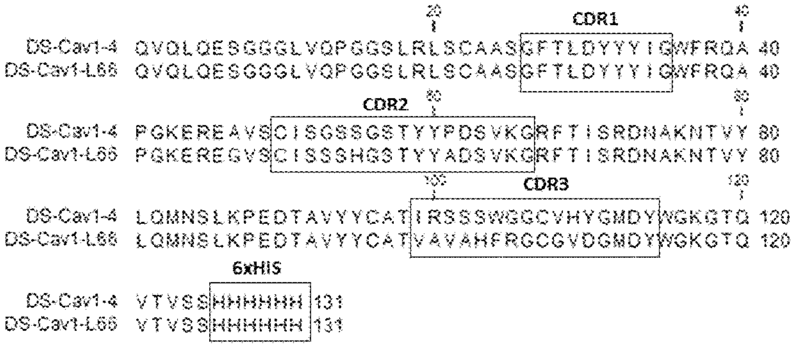

Figure 6
A
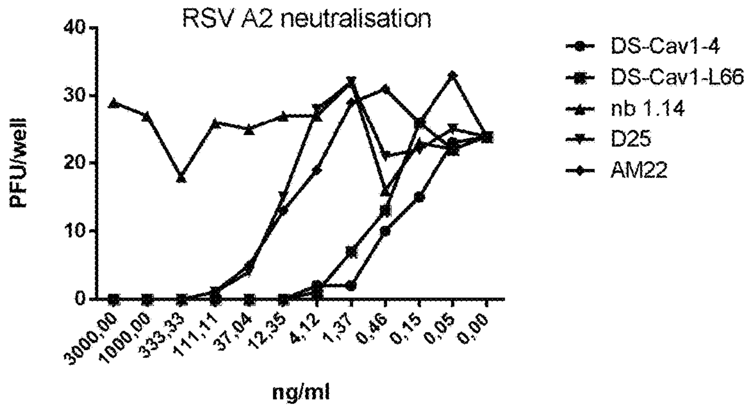
B
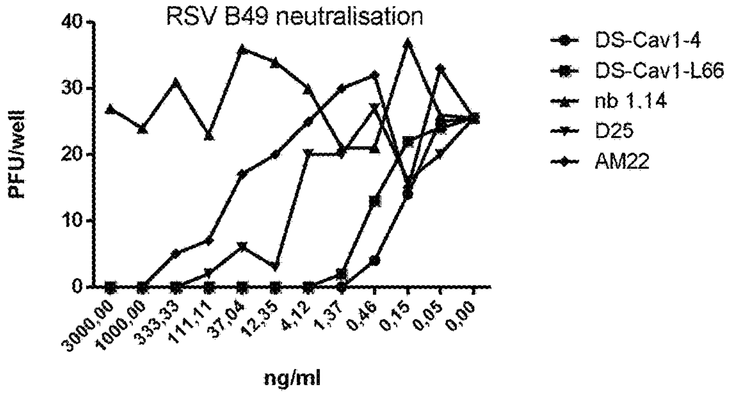

| | RSV A2 $IC_{50}$ | | RSV B49 $IC_{50}$ | |
|---|---|---|---|---|
| | ng/ml | nM | ng/ml | nM |
| DS-Cav1-4 | 0,31 | 0,021 | 0,23 | 0,015 |
| DS-Cav1-L66 | 0,46 | 0,032 | 0,46 | 0,032 |
| D25 | 18,5 | 0,123 | 8,24 | 0,055 |
| AM22 | 12,35 | 0,082 | 74,08 | 0,494 |

D

| $IC_{50}$ (ng/ml) | hMPV-A1-GFP | hMPV-B1-GFP | hRSV-A2-GFP |
|---|---|---|---|
| F-VHH-4 | >30,000 | >30,000 | 0.47 |
| F-VHH-L66 | >30,000 | >30,000 | 0.59 |
| Crtl-VHH | ND* | >30,000 | >30,000 |
| MPE8 | ND | 108 | 47 |
| 101F | 216 | 783 | 124 |
| MF14** | 249 | 319 | ND |
| Motavizumab | ND | ND | 33 |

*ND, not determined

**MF14 is a monoclonal antibody specific for the hMPV F glycoprotein

Figure 7
A
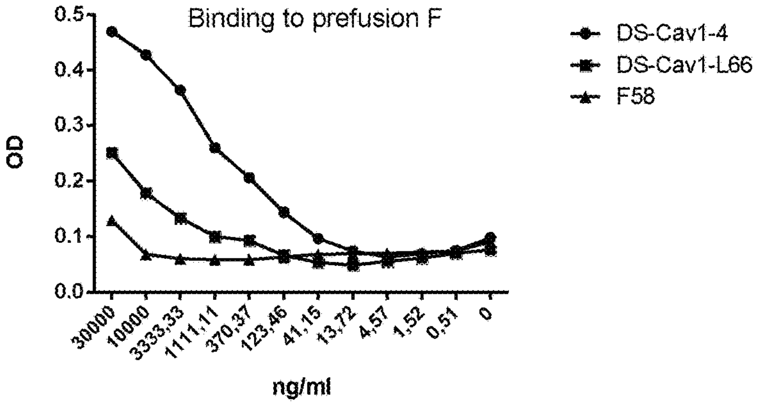
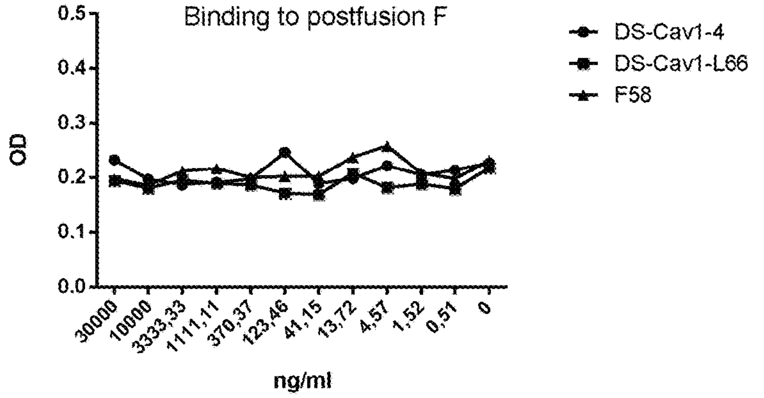

Figure 7 continued
B
Binding of DS-Cav1-4 to prefusion F
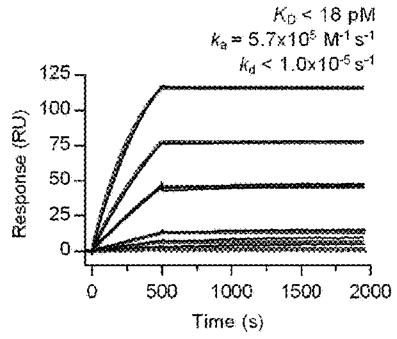
Binding of DS-Cav1-L66 to prefusion F
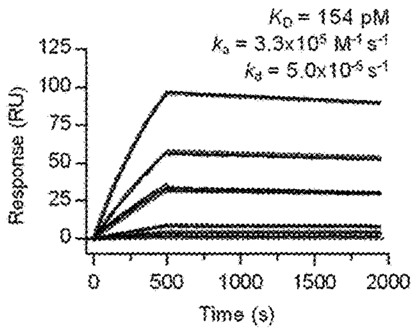
Binding of DS-Cav1-4 to postfusion F
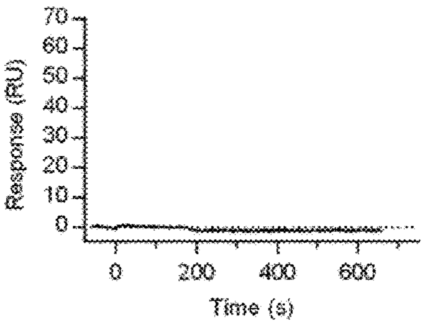
Binding of DS-Cav1-L66 to postfusion F
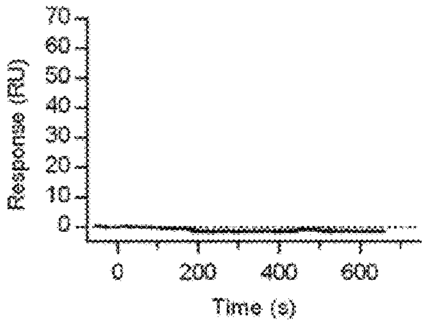

Figure 8
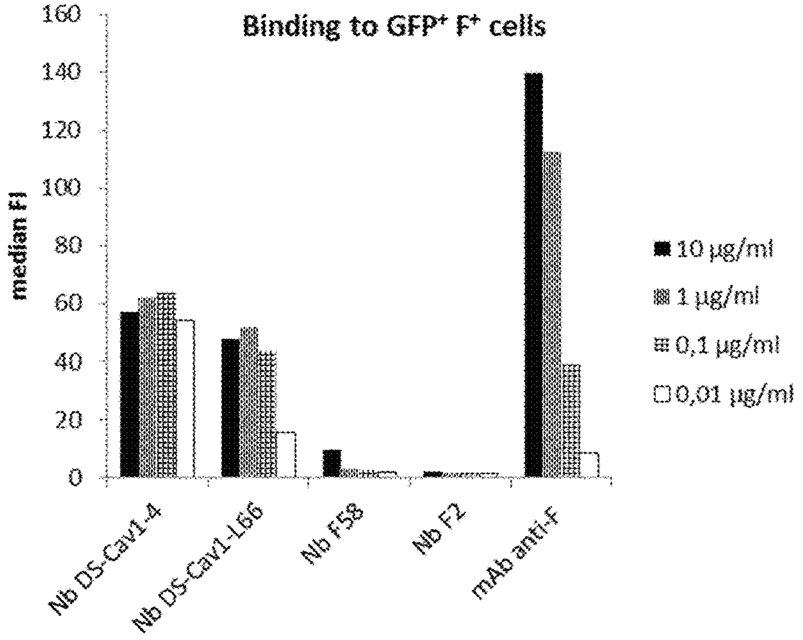
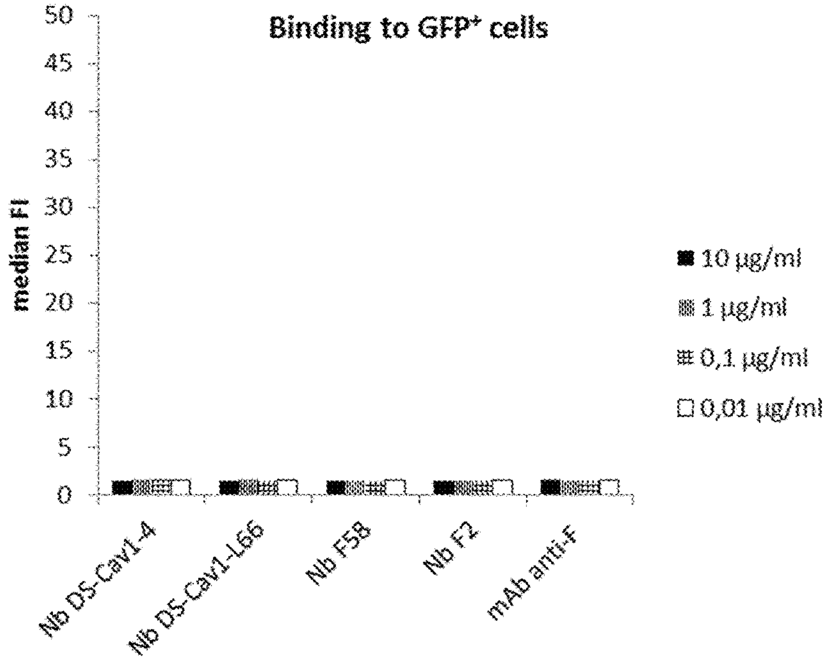

Figure 9
Analyte
| Competitor | F2 | DS-Cav1-L66 | DS-Cav1-4 | D25 |
|---|---|---|---|---|
| F2 | NB | 17.5 | 12.8 | 5.4 |
| DS-Cav1-L66 | NB | 82.1 | 58.3 | 11.7 |
| DS-Cav1-4 | NB | 105.0 | 81.7 | 18.3 |
| D25 | NB | 27.1 | 8.3 | 88.4 |
Figure 10
A
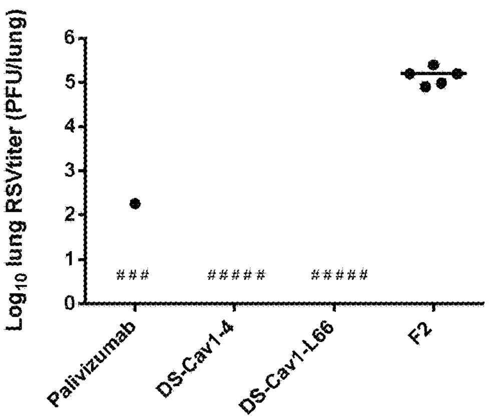
B
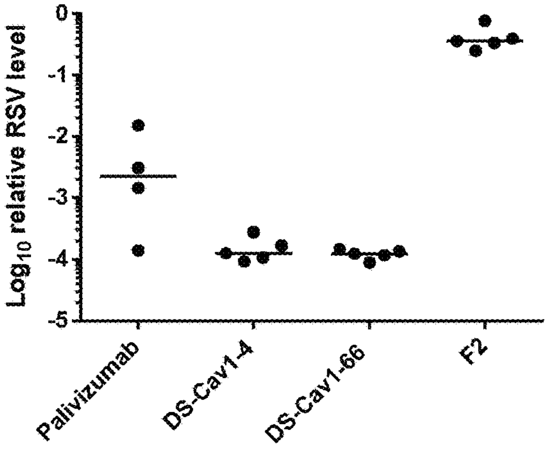

Rfree/Rwork: 27.7/19.4%

Buried Surface Area
On $F_2$ Protomer 1: 116 Å²
On $F_1$ Protomer 1: 640 Å²
On $F_1$ Protomer 2: 400 Å²
Total: 1156 Å²

Residues on RSV F contacted by nanobody

QNITEEFYQSTCSAVSKGYLSALRTGWYTSVITIELSNIKENKCNGTDAKVK
LIKQELDKYKNAVTELQLLMQSTPATNNRARR

FLGFLLGVGSAIASGVAVCKVLHLEGEVNKIKSALLSTNKAVVSLSNGVSVL
TFKVLDLKNYIDKQLLPILNKQSCSISNIETVIEFQQKNNRLLEITREFSVN
AGVTTPVSTYMLTNSELLSLINDMPITNDQKKLMSNNVQIVRQQSYSIMCII
KEEVLAYVVQLPLYGVIDTPCWKLHTSPLCTTNTKEGSNICLTRTDRGWYCD
NAGSVSFFPQAETCKVQSNRVFCDTMNSLTLPSEVNLCNVDIFNPKYDCKIM
TSKTDVSSSVITSLGAIVSCYGKTKCTASNKNRGIIKTFSNGCDYVSNKGVD
TVSVGNTLYYVNKQEGKSLYVKGEPIINFYDPLVFPSDEFDASISQVNEKIN
QSLAFIRKSDELL

B

Rfree/Rwork: 30.21/27.06%

Buried Surface Area
On $F_2$ Protomer 1: 116 Å²
On $F_1$ Protomer 1: 610 Å²
On $F_1$ Protomer 2: 450 Å²
Total: 1176 Å²

Residues on RSV F contacted by nanobody

QNITEEFYQSTCSAVSKGYLSALRTGWYTSVITIELSNIKENKCNGTDAKVK
LIKQELDKYKNAVTELQLLMQSTPATNNRARR

FLGFLLGVGSAIASGVAVCKVLHLEGEVNKIKSALLSTNKAVVSLSNGVSVL
TFKVLDLKNYIDKQLLPILNKQSCSISNIETVIEFQQKNNRLLEITREFSVN
AGVTTPVSTYMLTNSELLSLINDMPITNDQKKLMSNNVQIVRQQSYSIMCII
KEEVLAYVVQLPLYGVIDTPCWKLHTSPLCTTNTKEGSNICLTRTDRGWYCD
NAGSVSFFPQAETCKVQSNRVFCDTMNSLTLPSEVNLCNVDIFNPKYDCKIM
TSKTDVSSSVITSLGAIVSCYGKTKCTASNKNRGIIKTFSNGCDYVSNKGVD
TVSVGNTLYYVNKQEGKSLYVKGEPIINFYDPLVFPSDEFDASISQVNEKIN
QSLAFIRKSDELL

SEQ ID NO: 17:

```
1   MELLILKANA ITTILTAVTF CFASGQNITE EFYQSTCSAV SKGYLSALRT GWYTSVITIE
61  LSNIKENKCN GTDAKVKLIK QELDKYKNAV TELQLLMQST PATNNRARRE LPRFMNYTLN
121 NAKKTNVTLS KKRKRRFLGF LLGVGSAIAS GVAVCKVLHL EGEVNKIKSA LLSTNKAVVS
181 LSNGVSVLTF KVLDLKNYID KQLLPILNKQ SCSISNIETV IEFQQKNNRL LEITREFSVN
241 AGVTTPVSTY MLTNSELLSL INDMPITNDQ KKLMSNNVQI VRQQSYSIMC IIKEEVLAYV
301 VQLPLYGVID TPCWKLHTSP LCTTNTKEGS NICLTRTDRG WYCDNAGSVS FFPQAETCKV
361 QSNRVFCDTM NSLTLPSEVN LCNVDIFNPK YDCKIMTSKT DVSSSVITSL GAIVSCYGKT
421 KCTASNKNRG IIKTFSNGCD YVSNKGVDTV SVGNTLYYVN KQEGKSLYVK GEPIINFYDP
481 LVFPSDEFDA SISQVNEKIN QSLAFIRKSD ELLSAIGGYI PEAPRDGQAY VRKDGEWVLL
541 STFLGGLVPR GSHHHHHHSA WSHPQFEK
```

D

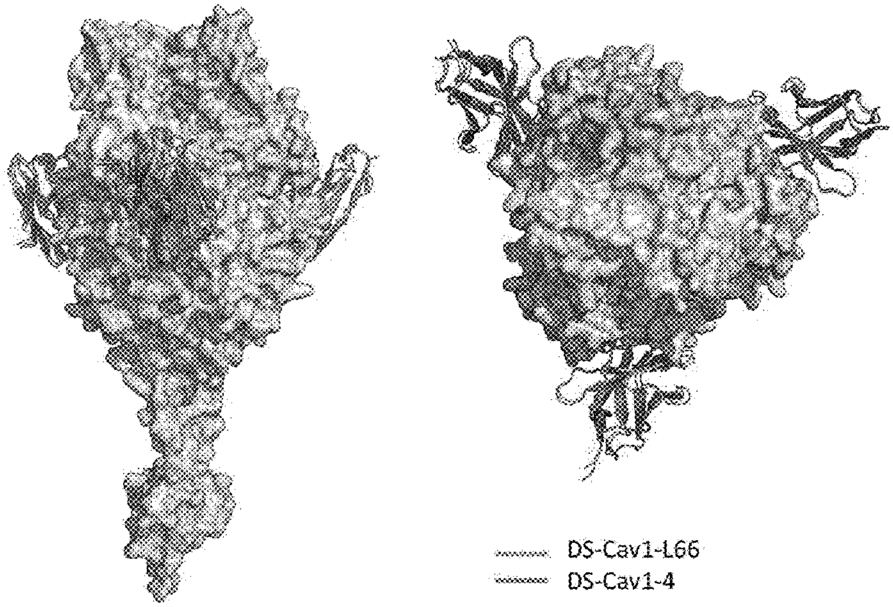

Figure 12
A
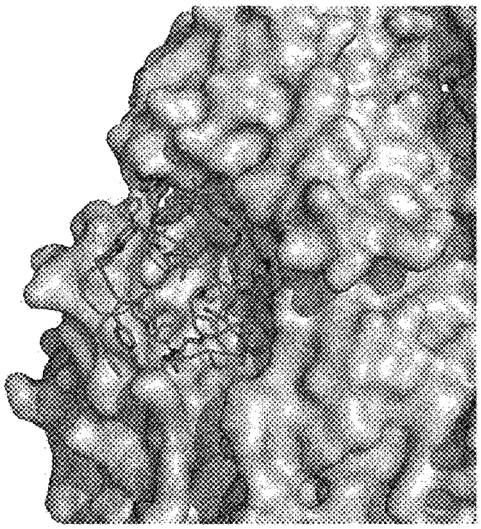
B
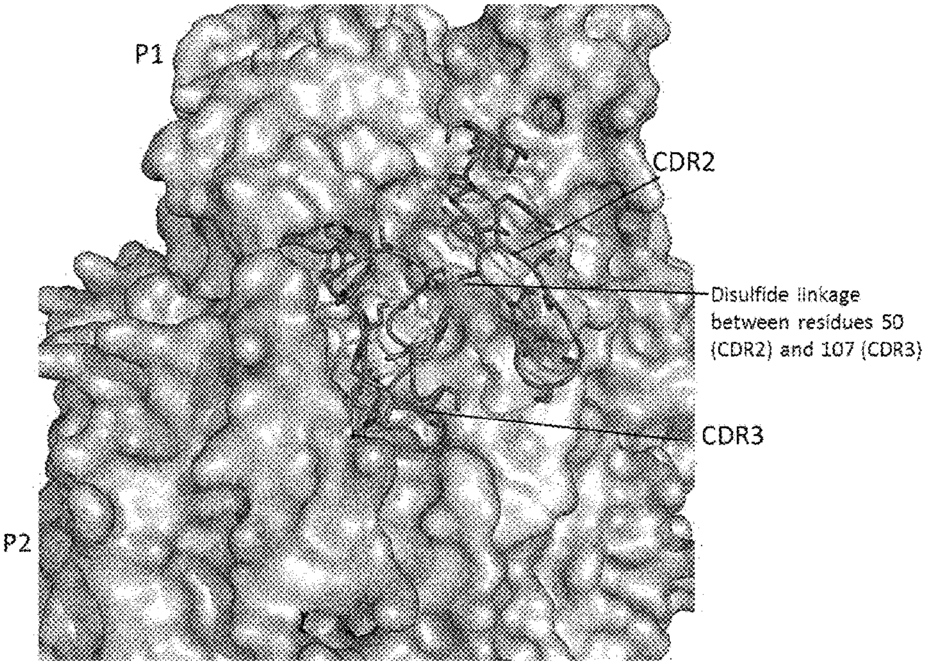

A

B

IMMUNOGLOBULIN SINGLE VARIABLE DOMAIN ANTIBODY AGAINST RSV PREFUSION F PROTEIN

RELATED APPLICATIONS

This application is a 35 U.S.C. § 371 filing of International Patent Application No. PCT/EP2016/064218, filed Jun. 20, 2016, which claims priority to U.S. Provisional Patent Application Ser. No. 62/181,522, filed Jun. 18, 2015, European Patent Application No. 15178653.0, filed Jul. 28, 2015, and European Patent Application No. 15191868.7, filed Oct. 28, 2015, the entire disclosures of which are hereby incorporated herein by reference in their entirety.

FIELD OF THE INVENTION

The present invention relates to immunoglobulin single variable domains (ISVDs) that are directed against respiratory syncytial virus (RSV). More specifically, it relates to ISVDs that bind to the prefusion form of the fusion (F) protein of RSV. The invention relates further to the use of these ISVDs for prevention and/or treatment of RSV infections, and to pharmaceutical compositions comprising these ISVDs.

BACKGROUND

Respiratory syncytial virus is the most important cause of acute airway infections in infants and young children. By the age of two nearly all children will have undergone at least one respiratory syncytial virus infection. Although usually causing only mild disease, in a fraction of patients (1-2%) RSV infection leads to serious bronchiolitis where hospitalization is required. It has been estimated that each year 160,000 children die due to RSV infection. No effective prophylactic vaccine and no RSV-specific therapeutic small molecule are clinically developed. The only way in which high-risk infants can be partially protected from a severe disease caused by an anticipated RSV infection is by monthly injections with a humanized mouse monoclonal antibody directed against the pre- and postfusion conformation of the F protein of RSV (palivizumab). Nevertheless, treatment with this antibody is expensive and only used in a prophylactic setting. Several other RSV F protein binding agents are being developed, including prefusion specific monoclonal antibodies (Gilmans et al., 2015; McLellan et al., 2013), and a RSV F protein binding ISVD. However, the described ISVD has weak neutralization activity against RSV serotype B and/or multivalent formatting is needed to render the ISVD potent (WO2009147248; WO2010139808; WO2011064382; Schepens et al., 2011; Hultberg et al., 2011).

Recently, it was shown that conventional antibodies that specifically bind to the prefusion conformation of the RSV F protein are much more potent in vitro RSV neutralizers than antibodies that bind both the post- and the prefusion conformation of F (WO2008147196, US2012070446, McLellan et al., 2013). However, conventional antibodies can be cumbersome to produce and their stability may be limited. Furthermore, due to their relatively large size conventional antibodies can be hindered in their cognate epitope recognition in complex samples or when other antibodies and ligands are occupying sites in the vicinity of their epitopes.

Accordingly, and as there is no widely accepted treatment available, there is an unmet need for a potent anti-RSV drug which can be used for effective treatment and/or prevention of RSV infections.

SUMMARY

It is surprisingly shown herein that monovalent ISVDs can have strong neutralization activity against both RSV serotypes (A and B). This is unexpected, as literature suggests that multivalent constructs are needed for potent inhibition of both serotypes of RSV. Accordingly, it is an object of the invention to provide ISVDs directed against epitopes of the RSV F protein that are unique to the prefusion conformation and thereby provide highly potent ISVDs for the treatment and/or prevention of RSV infections.

It is an aspect of the present invention to provide an ISVD that binds specifically to the prefusion form of the F protein of RSV, characterized in that said ISVD shows in monovalent format a similar neutralization activity of RSV serotypes A and B.

In one embodiment, the invention envisages an ISVD that comprises a CDR1 sequence selected from the group consisting of SEQ ID NO: 1 and SEQ ID NO: 2, a CDR2 sequence selected from the group consisting of SEQ ID NO: 3 and SEQ ID NO: 4 and a CDR3 sequence selected from the group consisting of SEQ ID NO: 5 and SEQ ID NO: 6 and wherein CDR1, CDR2 and/or CDR3 have a 1-, 2- or 3-amino acid difference with any of said foregoing respective SEQ ID NOs.

According to another aspect, the invention also relates to a RSV binding construct that comprises at least one ISVD as described above.

According to another aspect, the invention envisages a nucleic acid that encodes at least one ISVD as described above.

According to yet another aspect, the present invention relates to a host cell that is transformed or transfected with the nucleic acid as described above. Also envisaged is the use of the above described host cell for the production of the ISVD as described above.

Also envisaged is the ISVD as described above or the RSV binding construct as described above, for use as a medicament, in particular for use in therapeutic treatment or prevention of a RSV infection.

According to another aspect, the invention envisages a pharmaceutical composition that comprises at least one ISVD as described above. Further envisaged is the use of said pharmaceutical composition as a medicament, in particular in therapeutic treatment or prevention of a RSV infection.

Objects of the present invention will be clear from the description that follows.

BRIEF DESCRIPTION OF THE FIGURES

FIG. 1: Neutralizing activity in plasma from llama immunized with DS-Cav1. Neutralizing activity against RSV A2 (A) and RSV B49 (B) was tested in the plasma obtained after different immunizations with DS-Cav1. Monolayers of Vero cells seeded in 96-well plates were infected with RSV A2 or RSV B49 in the presence of llama plasma, threefold diluted as indicated in the X-axis and starting with eightfold dilution. The number of plaques in each well was counted and is depicted in the Y-axis. Pre DS-Cav 1 corresponds to the pre-immune serum of the immunized llama.

FIG. 5: Nucleotide sequences of VHH-DS-Cav1-4 (A) and VHH-DS-Cav1-L66 (B) and predicted amino acid sequences of recombinant VHH-DS-Cav1-4 and VHH-DS-Cav1-L66 produced in *P. pastoris* (C). The Complementarity Determining Regions (CDRs) and His tag (6×HIS) are indicated by labeled boxes.

FIG. 6: VHH-DS-Cav1-4 and VHH-DS-Cav1-166 have potent RSV neutralizing activity. Vero cells were infected with RSV A2 (A) or RSV B49 (B) in the presence of purified VHH (VHH-DS-Cav1-4, VHH-DS-Cav1-L66 or negative control NB 1.14), monoclonal antibody D25 or monoclonal antibody AM22. VHHs and monoclonal antibodies were applied in a threefold dilution series starting with a concentration of 3,000 ng/ml. The 50% inhibitory concentration (IC50) was calculated based on the plaque reduction shown in A and B and is depicted in (C). $IC_{50}$ values for F-VHH-4 (DS-Cav1-4) and F-VHH-L66 (DS-Cav1-L66) compared to Ctrl-VHH and mAbs against HMPV-A1-GFP, hMPV-B1-GFP and RSV A2-GFP (D). Pre-determined amounts of GFP-expressing hMPV recombinant viruses (NL/1/00 A1 sublineage or NL/1/99 B1 sublineage, a kind gift of Bernadette van den Hoogen and Ron Fouchier, Rotterdam, the Netherlands) or GFP-hRSV (A2 strain, a kind gift of Mark Peeples, Columbus, Ohio, USA) (MOI 0.3 ffu/cell) were mixed with serial dilutions of VHHs or mAbs and added to cultures of either Vero-118 (hMPV) or HEp-2 cells, growing in 96-well plates. Thirty-six hours later, the medium was removed, PBS was added and the GFP fluorescence in each well was measured with a Tecan microplate reader M200. Fluorescence values were plotted as percent of a virus control without antibody and used to calculate the corresponding $IC_{50}$ values.

FIG. 7: VHH-DS-Cav1-4 and VHH-DS-Cav1-166 bind to DS-Cav1 but not to postfusion F. (A) ELISA plates were coated with DS-Cav1 (upper panel) or postfusion F (lower panel). The plates were incubated with a 1/3 dilution series of purified VHH-DS-Cav1-4, VHH-DS-Cav1-L66 and VHH-F58 starting from 30,000 ng/ml. The OD450 values are depicted. (B) Surface plasmon resonance (SPR) sensorgrams of the binding of VHH-DS-Cav1-4 and VHH-DS-Cav1-L66 to immobilized prefusion or postfusion F protein. In the top panel, depicting SPR sensorgrams for prefusion F, a buffer-only sample was injected over the DS-Cav1 (prefusion F) and reference flow cells, followed by 2-fold serial dilutions of VHH-DS-Cav1-4 or VHH-DS-Cav1-L66 ranging from 5 nM to 39.1 pM, with a duplication of the 1.25 nM concentration. The data were double-reference subtracted and fit to a 1:1 binding model (red lines). The lower panels depict SPR sensorgrams for binding of VHH-DS-Cav1-4 and VHH-DS-Cav1-L66 to immobilized postfusion F. A buffer-only sample was injected over the postfusion F and reference flow cells, followed by 1 μM and 500 nM concentrations of DS-Cav1-4 or DS-Cav1-L66. The data were double-reference subtracted, but were not fit to a binding model, as no binding to postfusion F was detected.

FIG. 8: VHH-DS-Cav1-4 and VHH-DS-Cav1-166 bind to F on the surface of mammalian cells. HEK-293T cells were transfected with a RSV A2 F protein expression vector (pCAGGS-Fsyn) in combination with a GFP-NLS expression vector (peGFP-NLS) or transfected with only the GFP-NLS expression vector. The graph shows the median fluorescence intensity (FI) of the indicated VHHs and an RSV F specific mouse monoclonal antibody (MAB858-1, Millipore) to GFP positive cells expressing either the RSV F protein (top graph) or not (bottom graph).

FIG. 9: Antibody cross-competition on DS-Cav1-binding analyzed by using biolayer interferometry. DS-Cav1 was immobilized on AR2G biosensors through amine coupling reaction in acetate buffer. The reaction was quenched by 1M ethanolamine and DS-Cav1-immobilized biosensors were then equilibrated with assay buffer (PBS with 1% BSA). The biosensors were dipped in competitor antibodies/VHHs followed by analyte antibodies/VHHs with a short baseline step in between two antibody/VHH steps. Percent inhibitions were defined by comparing binding maxima of the analyte antibody/VHH in the absence and presence of each competitor. NB: no binding.

FIG. 10: Prophylactic administration of DS-Cav1-4 and DS-Cav1-166 reduces RSV replication in vivo. 30 μg of DS-Cav1-4, DS-Cav1-L66 or F2, and 30 μg of palivizumab was administered intranasally to BALB/c mice four h prior to challenge with RSV A2. Twenty four h after infection all mice received 30 μg of F2 intranasally. Mice were sacrificed on day five after challenge and the virus load in the lungs was determined by plaque assay (A) and by qRT-PCR (B). Each data point represents one mouse and the horizontal lines depict the median. #: Mouse with virus titer in lung homogenate below detection limit. Graph (B) represents the relative expression of RSV RNA, normalized to mRPL13A mRNA levels present in the samples of each mouse in the indicated groups.

FIG. 11: VHH-DS-Cav1-4 and VHH-DS-Cav1-166 bind the same epitope on RSV F, with high structural conservation. (A) Buried Surface Area and Residues on prefusion-stabilized RSV F (SEQ ID NO: 16) that are contacted by VHH-DS-Cav1-4 (shown in bold). (B) Buried Surface Area and Residues on prefusion-stabilized RSV F (SEQ ID NO: 16) that are contacted by VHH-DS-Cav1-L66 (shown in bold). (C) The amino acid residues of the prefusion-stabilized RSV F protein full open-reading frame, before in vivo processing (SEQ ID NO: 17) that are contacted by both, VHH-DS-Cav1-4 and VHH-DS-Cav1-L66, are shown underlined. (D) Co-crystal structure of both ISVDs with RSV prefusion F protein shows high structural conservation of the ISVDs and binding to the same epitope.

FIG. 12: Binding specifics of VHH-DS-Cav1-4. (A) CDR3 loop of VHH-DS-Cav1-4 binds to a pocket formed by two protomers of RSV F. (B) CDR2 loop of VHH-DS-Cav1-4 interacts with site II and is joined to CDR3 through a disulfide bond. P1=protomer 1; P2=protomer 2.

DETAILED DESCRIPTION

Definitions

Figure 2:
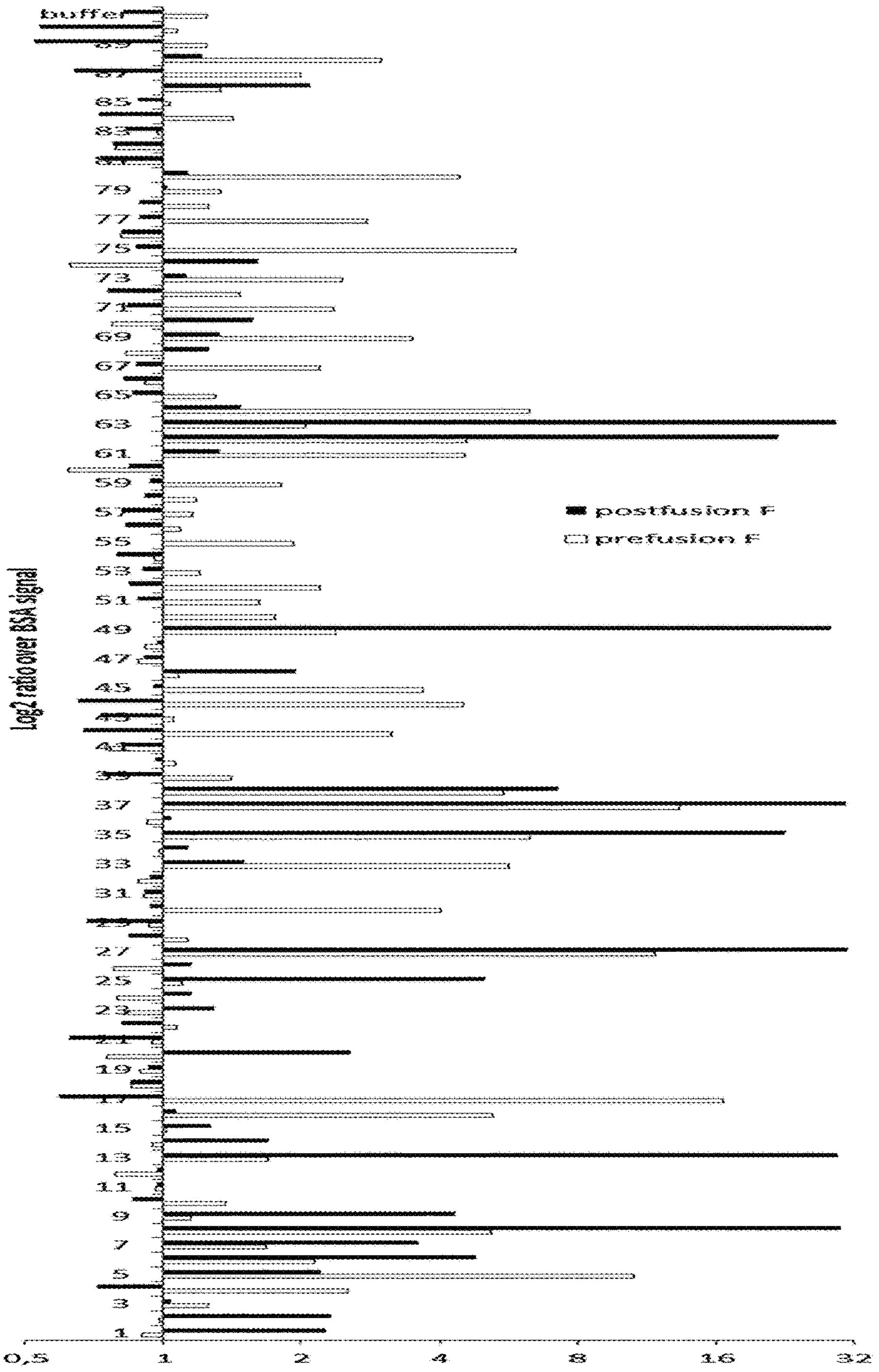
FIG. 2: Selection of VHHs that bind to purified recombinant RSV fusion protein (F). ELISA plates were coated with DS-Cav1 (grey bars, prefusion F), postfusion F (black bars) or BSA. The plates were incubated with bacterial periplasmic space extracts prepared from pHEN4-VHH transformed TG1 *E. coli* cells that had been obtained after one round of panning against DS-Cav1 with the VHH-displaying phage library generated from the PBMCs of the DS-Cav1 immunized llama. In the graph, the binding to the F protein is depicted as the log 2 ratio of OD450 values over binding to BSA.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

An "immunoglobulin single variable domain" or "ISVD" is an antibody fragment consisting of a single variable antibody domain. Like a whole antibody, it is able to bind selectively to a specific antigen. With a molecular weight of only 12-18 kDa, ISVDs are much smaller than conventional antibodies (150-160 kDa) which are composed of two heavy and two light protein chains, and even smaller than Fab fragments (~50 kDa, one light chain and half a heavy chain) and single chain variable fragments (~25 kDa, two variable domains, one from a light and one from a heavy chain). Generally, an ISVD will have an amino acid sequence comprising 4 framework regions (FR1 to FR4) and 3 complementarity determining regions (CDR1 to CDR3), preferably according to the following formula: FR1-CDR1-FR2-CDR2-FR3-CDR3-FR4. The term "ISVD", as used herein, includes—but is not limited to—variable domains of camelid heavy chain antibodies (VHHs), also referred to as Nanobodies™, domain antibodies (dAbs), and ISVDs derived from shark (IgNAR domains).

The term "binds specifically to the prefusion form of the F protein of RSV", as used herein, refers to the ability of a RSV binding polypeptide (e.g. an antibody, an ISVD) to measurably bind to the prefusion form of the F protein of RSV and not to the postfusion from of the F protein of RSV.

The "prefusion form of the F protein of RSV" refers to the metastable prefusion conformation of the RSV F protein, that is adopted before virus-cell interaction, as described in McLellan et al., 2013. It is distinct from the highly stable postfusion form or postfusion conformation, which is adopted upon fusion of the viral and cellular membranes.

The "monovalent format" of an antibody as used herein refers to an antibody format that can only recognize one antigenic determinant. It excludes multivalent antibody formats that can recognize more than one antigenic determinant, such as—but not limited to—bivalent, trivalent or tetravalent formats.

The term "neutralization activity" as used herein, refers to the fact that the ISVD can inhibit virus infection as measured in an in vitro virus neutralization assay, such as—but not limited to—a plaque reduction assay. Neutralization, also referred to as inhibition, can mean full neutralization (no virus infection is observable) or may mean partial neutralization. For instance, neutralization can mean 10% neutralization, 20% neutralization, 25% neutralization, 30% neutralization, 40% neutralization or more. Particularly, neutralization will be at least 50%, e.g. 50% neutralization, 60% neutralization, 70% neutralization, 75% neutralization, 80% neutralization, 90% neutralization, 95% neutralization or more. The neutralization activity typically will be evaluated against a suitable control (e.g. treatment with an irrelevant ISVD), as will be readily chosen by the skilled person. For ISVDs with known concentration, the neutralization activity can be expressed as 50% inhibitory concentration (IC50). The IC50 is the ISVD concentration at which 50% inhibition (or neutralization) is achieved. It is a measure of the inhibitory potential, also referred to as potency, of an ISVD.

A "similar neutralization activity" as used herein, refers to a neutralization activity, expressed as IC50, that typically differs ten-fold or less from the neutralization activity it is compared to. More particularly, it differs five-fold or less, or even two-fold or less.

The term "complementarity determining region" or "CDR" refers to a variable loop within the variable regions of either H (heavy) or L (light) chains of immunoglobulins and contains the amino acid sequences capable of specifically binding to antigenic targets. These CDR regions account for the basic specificity of an antibody or antibody fragment for a particular antigenic determinant structure.

The term "epitope" refers to a specific binding site on an antigen or on an antigenic structure for which a polypeptide, such as an ISVD, has specificity and affinity.

The term "conformational epitope" refers to an epitope with the three-dimensional surface features of an antigen, allowing to fit precisely and bind a polypeptide, such as an ISVD. In contrast, linear epitopes are determined by the amino acid sequence (primary structure) rather than by the 3D shape (tertiary structure) of a protein.

"Therapeutic treatment of a RSV infection", as used herein, means any form of treatment of a RSV infection that is administered to a subject after said subject contracted a RSV infection.

"Prevention of a RSV infection", as used herein, means a prophylactic treatment of a RSV infection that is administered to a subject before said subject contracted a RSV infection. Prophylactic treatment may include the use of the present invention as a vaccine.

A "pharmaceutical composition", as used herein, may be any pharmaceutical composition known to the person skilled in the art, including, but not limited to compositions for systemic, oral and intranasal delivery.

A "RSV binding construct that comprises at least one ISVD", as used herein, refers to any binding construct that binds to RSV and comprises one or more ISVDs.

A "host cell", as used herein, may be any cell that is suitable for production of ISVDs or RSV binding constructs.

According to a first aspect, it is an objective of the invention to provide ISVDs that are directed against and/or bind specifically to the prefusion form of the F protein of RSV. Specific binding to the prefusion form of the F protein of RSV means that the ISVD measurably binds to the prefusion form of the F protein of RSV and not to the postfusion form of the F protein of RSV. Specific binding can be influenced by, for example, the affinity of the ISVD and the concentration of the ISVD. The person of ordinary skill in the art can determine appropriate conditions under which the binding ability of the ISVD described herein can be evaluated, such as titration of the ISVD in a suitable binding assay, such as—but not limited to—an enzyme-linked immunosorbent assay (ELISA), or a binding assay based on surface plasmon resonance (SPR) or biolayer interferometry (BLI). Typically, binding to the prefusion form of the F protein of RSV means that the ISVD binds to the wild type form of the F protein as well as to any mutant form of the F protein, as long as the F protein is in the prefusion conformation. It also includes binding to the F protein of both subtypes (A and B) of RSV. In a particular embodiment, above described ISVD binds to the RSV A F protein consensus sequence as set forth in SEQ ID NO: 18. The consensus sequence set forth in SEQ ID NO: 18 was calculated with methods known to the skilled artisan based on 92 RSV A F protein full length sequences listed in the NCBI protein database. Therefore, above described ISVD binds to any of the 92 representative RSV A F protein sequences included to derive to the consensus sequence of SEQ ID NO: 18. In a particular embodiment, above described ISVD binds to the RSV B F protein consensus sequence as set forth in SEQ ID NO: 19. The consensus sequence set forth in SEQ ID NO: 19 was calculated with methods known to the skilled artisan based on 114 RSV B F protein full length sequences listed in the NCBI protein database. Therefore, above described ISVD binds to any of the 114 representative RSV B F protein sequences included to derive to the consensus sequence of SEQ ID NO: 19. In a particular embodiment, above described ISVD binds to both, RSV A F protein as set forth in SEQ ID NO: 18 and RSV B F protein as set forth in SEQ ID NO: 19. In a particular embodiment, above described ISVDs bind exclusively to the prefusion form of the F protein. According to further particular embodiments, above mentioned ISVDs bind exclusively to the prefusion form of the F protein and do not bind to the postfusion form of the F protein. In a particular embodiment, above described ISVDs bind to the prefusion-stabilized RSV F protein of SEQ ID NO: 16. In a particular embodiment, the ISVD may be fused to further moieties.

According to particular embodiments, above described ISVDs bind to an epitope of the RSV prefusion F protein. In particular, they bind to a conformational epitope of the RSV prefusion F protein. In a particular embodiment, above described ISVDs bind a RSV prefusion F conformational epitope comprising amino acid residues T50, G51, W52, S180, G184, V185, P265, I266, T267, N268, D269, Q270, L305, G307, V308, N345, A346, G347, K421, S425, K427, N428, R429, G430, I431, S451, G453, N454, L456, Y458. In particular they bind a RSV prefusion F conformational epitope comprising amino acid residues T50, G51, W52, S180, G184, V185, P265, I266, T267, N268, D269, Q270, L305, G307, V308, N345, A346, G347, K421, S425, K427, N428, R429, G430, I431, S451, G453, N454, L456, Y458 of RSV prefusion F as set forth in SEQ ID NO: 17.

According to particular embodiments, the ISVD shows in monovalent format a similar neutralization activity of RSV serotypes A and B. Typically, that means that the ISVD interferes with/inhibits/prevents/reverses or slows the ability of the virus to infect a cell. According to these particular embodiments, the ISVD interferes with/inhibits/prevents/reverses or slows the ability of the virus to infect a cell to a similar extent for both the A and B RSV serotypes.

According to particular embodiments, the ISVD comprises a CDR1 sequence selected from the group consisting of SEQ ID NO: 1 and SEQ ID NO: 2, a CDR2 sequence selected from the group consisting of SEQ ID NO: 3 and SEQ ID NO: 4 and a CDR3 sequence selected from the group consisting of SEQ ID NO: 5 and SEQ ID NO: 6, wherein CDR1, CDR2 and/or CDR3 have a 1-, 2- or 3-amino acid difference with any of said foregoing respective SEQ ID NOs. For the ISVD DS-Cav1-4, the sequences of the CDRs are SEQ ID NO: 1, SEQ ID NO: 3 and SEQ ID NO: 5. For the ISVD DS-Cav1-L66 the sequences of the CDRs are SEQ ID NO: 2, SEQ ID NO: 4 and SEQ ID NO: 6.

According to a further aspect, a RSV binding construct is provided, characterized in that said RSV binding construct comprises at least one ISVD. At least one ISVD means that the RSV binding construct may contain more than one ISVD. Next to the one or more ISVDs, the RSV binding construct may contain other moieties linked to the ISVD. Said further moieties may bind to RSV or not. As a non-limiting example, said RSV binding construct may comprise an ISVD that binds to RSV F protein and may be linked (chemically or otherwise) to one or more groups or moieties that extend the half-life (such as—but not limited to—polyethylene glycol (PEG) or a serum albumin binding VHH), so as to provide a derivative of an ISVD of the invention with increased half-life. Typically, said RSV binding construct binds to the RSV prefusion F protein. In a particular embodiment, above described RSV binding construct binds to SEQ ID NO: 17 and/or SEQ ID NO: 18 and/or SEQ ID NO: 19. Said RSV binding construct may be any construct comprising one or more than one RSV binding ISVD.

According to a further aspect, the ISVDs are not provided as such, but are provided as nucleic acid, i.e. nucleic acid molecules encoding ISVDs against the RSV F protein as herein described, particularly against the prefusion form of the F protein. Also provided are vectors comprising such nucleic acids or nucleic acid molecules. According to yet a further aspect, host cells are provided comprising such nucleic acids or such vectors. Typically, the nucleic acids will have been introduced in the host cell by transfection or transformation, although the way in which the nucleic acid is introduced in the host cell is not limiting the invention.

According to yet further embodiments, host cells are provided containing such nucleic acids. Typically, such host cells will have been transformed or transfected with the nucleic acids. A particular use that is envisaged for these host cells is the production of the ISVDs. Thus, such use for production is explicitly envisaged herein. That means that host cells transformed or transfected with the nucleic acid molecules encoding ISVDs can be used for production of the ISVDs.

According to a further aspect, the ISVDs provided herein are for use in medicine. That is to say, the ISVDs against RSV F protein are provided for use as a medicament. The same goes for the nucleic acid encoding the ISVDs, or for the vectors containing such nucleic acids, i.e. it is envisaged that nucleic acid molecules or vectors encoding the ISVDs are provided for use as a medicament. Also the RSV binding constructs comprising at least one ISVD that binds to RSV F protein are provided for use as a medicament. According to particular embodiments, the ISVDs (or RSV binding constructs comprising them or pharmaceutical compositions comprising them or nucleic acids encoding them, or vectors comprising such nucleic acids) are provided for use in treatment or prevention of a RSV infection. This is equivalent as saying that methods are provided for treatment or prevention of a RSV infection for a subject in need thereof, comprising administering an ISVD against RSV F protein to said subject. Here also, the ISVD may be provided as protein (as single domain protein, as part of a RSV binding construct or pharmaceutical composition) or may be administered as a nucleic acid molecule encoding an ISVD against RSV F protein, or as a vector comprising such nucleic acid molecule. If the ISVD (or the RSV binding construct) is administered as protein, different routes of administration can be envisaged. As non-limiting examples, the ISVD may be administered systemically, orally or intranasally, such as e.g. through nasal inhalation. In case the ISVD is provided as a nucleic acid or vector, it is particularly envisaged that the ISVD is administered through gene therapy.

According to a further aspect, pharmaceutical compositions are provided comprising at least one ISVD directed to RSV prefusion F protein. Typically, such pharmaceutical compositions comprise at least one ISVD directed to the prefusion form of RSV F protein. Said pharmaceutical compositions may comprise further moieties. Said further moieties may bind to RSV or not. It is envisaged herein that the pharmaceutical compositions are provided for use as a medicament. Particularly, they are provided for use in therapeutic treatment or prevention of RSV infections. This is equivalent as stating that methods are provided for therapeutic treatment or prevention of RSV infections for a subject in need thereof, comprising administering a pharmaceutical composition as described herein to said subject.

According to further embodiments, a method is provided of therapeutic treatment or prevention of a RSV infection, the method comprising administering to a subject in need thereof the ISVD as described above, the RSV binding construct as described above or the pharmaceutical composition as described above. Said method comprises administering to said subject an ISVD against RSV prefusion F protein. Such methods typically will results in improvement or prevention of symptoms of the infection in said subject. Here also, the ISVD may be provided as protein (as single domain protein, as part of a RSV binding construct or pharmaceutical composition) or may be administered as a nucleic acid molecule encoding an ISVD against RSV F protein, or as a vector comprising such nucleic acid molecule, or as a pharmaceutical composition containing such antibody. Also, RSV binding constructs as described herein are envisaged for administration to a subject in need thereof in methods for therapeutic treatment or prevention of RSV infections.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Materials and Methods to the Examples

Immunization and VHH Library Generation

A llama was injected subcutaneously on days 0, 7, 14, 21, 28 and 35, each time with 167 μg of purified RSV F protein DS-Cav1. DS-Cav1 is a recombinant RSV F protein stabilized in the prefusion conformation (McLellan et al., 2013). The first two injections were performed with poly-IC (375 μg per injection) as adjuvant, while Gerbu LQ #3000 was used as adjuvant for the last four injections. Before every immunization blood was taken and plasma prepared to evaluate seroconversion. On day 40, 100 ml of anticoagulated blood was collected for the preparation of lymphocytes.

Total RNA from peripheral blood lymphocytes was used as template for first strand cDNA synthesis with oligodT primer. Using this cDNA, the VHH encoding sequences were amplified by PCR, digested with PstI and NotI, and cloned into the PstI and NotI sites of the phagemid vector pHEN4. Electro-competent *E. coli* TG1 cells were transformed with the recombinant pHEN4 vector resulting in a VHH library of about 5×108 independent transformants. 87% of the transformants harbored the vector with the right insert size, as evidenced by PCR analysis of 95 independent transformants. 500 μl of the library stock was infected with VCS M13 helper phage in order to display the VHH sequences (in fusion with M13 PIII) on the phage surface, which were used for bio-panning.

Cells

Hep-2 cells (ATCC, CCL-23), Vero cells (ATCC, CCL-81) and HEK-293T cells (a gift from Dr M. Hall) were grown in DMEM medium supplemented with 10% heat-inactivated fetal calf serum (FCS), 2 mM L-glutamine, non-essential amino acids (Invitrogen, Carlsbad, Calif.) and 1 mM sodium pyruvate.

Viruses

RSV A2 (VR-1540, ATCC, Rockville), an A subtype of RSV, and RSV B49, a B subtype of RSV (BE/5649/08 clinical strain, obtained from Prof M. Van Ranst, Tan et al., 2013) were propagated by infecting monolayers of Hep-2 cells, with 0.1 MOI in the presence of growth medium containing 1% FCS. Five days after infection the cells and growth medium were collected, pooled and clarified by centrifugation (450×g). To concentrate the virus, the clarified supernatant was incubated for four h at 4° C. in the presence of 10% polyethylene glycol (PEG6000). After centrifugation (30 minutes at 3000×g), the pellet was resuspended in Hank's balanced salt solution (HBSS), containing 20% sucrose, aliquoted, snap-frozen in liquid nitrogen and stored at −80° C.

RSV-Neutralizing Activity Assay

The llama plasma was tested for neutralizing activity against RSV A2 and RSV B49 by plaque assay. Vero cells were seeded in a 96-well plate (15000 cells/well). The next day, a dilution series of the plasma samples was prepared in Opti-MEM (Gibco) supplemented with 1% penicillin and 1% streptomycin (1/3 dilution series, starting with a 1/4 dilution). An equal volume of RSV A2 suspension (diluted to 1.4 PFU/μl) or RSV B49 (diluted to 2.8 PFU/μl) was added to the plasma samples and the obtained mixtures were incubated for 30 minutes at 37° C. Subsequently, 50 μl of the mixtures was added to the Vero cells, which had been washed with Opti-MEM, and the cells were incubated at 37° C. for three h. Next, 50 μl of 1.2% avicel in DMEM medium supplemented with 2% heat-inactivated FCS, 2 mM L-glutamine, non-essential amino acids and 1 mM sodium pyruvate was added to each well and the infection was allowed to continue at 37° C. for three days. The cells were fixed for 30 minutes at room temperature by adding 50 μl of a 2% paraformaldehyde solution to the wells. After fixation, the cells were washed twice with phosphate-buffered saline (PBS), permeabilized with 50 μl PBS with 0.2% Triton X-100 for 10 minutes and blocked with PBS containing 1% BSA. Subsequently, polyclonal goat anti RSV serum (AB1125, Chemicon International) was added (1/2000 in PBS containing 0.5% BSA and 0.001% Triton X-100 (PBS/BSA)). After three washes with PBS/BSA the cells were incubated with horseradish peroxidase-conjugated anti-goat IgG (SC2020, Santa Cruz) for 30 minutes. The wells were subsequently washed four times with PBS/BSA and once with PBS. Finally, the plaques were visualized by applying TrueBlue peroxidase substrate (KPL, Gaithersburg). RSV neutralizing activity in crude *Pichia pastoris* supernatant and of purified VHHs (see below) was also determined with this assay.

Isolation of DS-Cav1 Binding VHHs

We performed one round of panning to enrich for prefusion F (DS-Cav1) binding phages. One well (well A1) on a microtiter plate (type II, F96 Maxisorp, Nunc) was coated overnight with 20 μg DS-Cav1 in PBS. This well, along with an uncoated, negative control well (well A12) was blocked with SEA BLOCK blocking buffer (Thermo Scientific) for one h. Next, 1012 phages in a volume of 100 μl SEA BLOCK blocking buffer were added to these two wells. After one h, the unbound phage particles were removed and the wells were washed ten times with PBST (PBS+0.5% Tween20). The retained phages were then eluted by applying an alkaline solution consisting of 100 μl of TEA-solution (14% triethylamine (Sigma) pH 10) to the wells for exactly ten minutes. The dissociated phages were then transferred to a sterile tube with 100 μl 1M TRIS-HCl pH 8.0. Tenfold serial dilutions in PBS were prepared with the eluted phages, and 10 μl of this dilution series was used to infect 90 μl of TG1 cells (phage display competent *E. coli* cells). Infection was allowed for 30 minutes at 37° C., after which the bacteria were plated on LB/agar plates with 100 μg/ml ampicillin and 1% glucose. The enrichment for antigen-specific phages by this panning procedure was assessed by comparing the number of phagemid particles eluted from antigen-coated well with the number of phagemid particles eluted from the negative control well.

Ninety ampicillin resistant colonies were randomly selected for further analysis by ELISA for the presence of F-specific VHHs in their periplasm. These colonies were first transferred to a fresh LB agar plate with ampicillin and then used to inoculate 1 ml of Terrific Broth (TB) medium with 100 μg/ml ampicillin in a 24 deep well plate. Inoculated plates were incubated at 37° C. while shaking for five h. VHH expression was induced by adding isopropyl β-D-1-thiogalactopyranoside (IPTG) until a concentration of 1 mM. The plates were subsequently incubated overnight at 37° C. while shaking. The next day, bacterial cells were pelleted by centrifugation (12 minutes at 3200 rpm) and the supernatant was removed. The cell pellet was resuspended in 200 μl TES buffer (0.2 M TRIS-HCl pH 8, 0.5 mM EDTA, 0.5 M sucrose) and the plates were shaken at 4° C. for 30 minutes. Next, water was added to the resuspended cells to induce an osmotic shock, which leads to the release of the periplasmic proteins that include VHHs. The deep well plates were incubated for one h at 4° C. while shaking, centrifuged and the supernatant, containing the periplasmic extract was recovered. Four microtiter plates were coated overnight with 100 ng of protein per well in PBS, two with alternating rows of F in the postfusion conformation (McLellan et al., 2011) and BSA, two others with alternating rows of DS-Cav1 and BSA. The coated microtiter plates were then washed and blocked with 1% milk powder in PBS. After washing of the microtiter plates, 100 μl of periplasmic extract was added to the wells and followed by incubation for one h at 4° C. The plates were washed and 50 μl of a 1/2000 dilution of anti-HA (MMS-101P Biolegend) monoclonal antibody in PBS was added to the plate for one h at room temperature. After washing, a 1/2000 dilution in PBS of horseradish peroxidase (HRP)-linked anti-mouse IgG (NXA931, GE Healthcare) was added and the plates were incubated during one hour. Next, the plates were washed and 50 μl of TMB substrate (Tetramethylbenzidine, BD OptEIA™) was added to every well. The reaction was stopped by addition of 50 μl of 1M H2SO4 after which the absorbance at 450 nM was measured with an iMark Microplate Absorbance Reader (Bio Rad). All periplasmic fractions for which the OD450 values obtained for DS-Cav1 or postfusion F were at least two times higher than the OD450 values obtained for BSA, were selected for further analysis. The corresponding bacteria were grown in 3 ml of LB medium with 1/2000 ampicillin for plasmid isolation using the QIAprep Spin Miniprep kit (Qiagen). The cDNA sequence of the cloned VHH was determined by Sanger sequencing using M13RS primer (5'CAGGAAACAGCTATGACC3' (SEQ ID NO: 11)).

Cloning of VHH into *Pichia pastoris* Expression Vector and Transformation of *Pichia pastoris*

The VHH sequences, as well as the VHH sequences that were retained after the panning, were PCR amplified from the respective pHEN4 plasmids using the following forward and reverse primers (5'GGCGGGTATCTCTCGAGAAAAGGCAGGTGCAGCTGCAGGAGTCTGGG3' (SEQ ID NO: 12); 5'CTAACTAGTCTAGTGATGGTGATGGTGGTGGCTGGAGACGGTGACCTGG3' (SEQ ID NO: 13)). The resulting PCR products were digested with XhoI and SpeI and ligated into XhoI/SpeI digested pKai61 backbone. The origin of the pKai61 vector is described in Schoonooghe et al., 2009. The VHH sequences are cloned in frame with a slightly modified version of the *S. cerevisiae* a-mating factor signal sequence. This signal sequence directs the proteins to the yeast secretory system, is further processed in the ER and the golgi and will be fully removed before secretion into the extracellular medium. In contrast to the wild-type prepro signal, this modified version does not contain sequences that code for the GluAla repeats (here the signal peptide is efficiently cleaved by the Kex2 endopeptidase without the need for this repeat). The encoded genes contain a C-terminal 6×His tag and are under control of the methanol inducible AOX1 promoter. The plasmid contains a Zeocine resistance marker for selection in bacterial as well as in yeast cells. The vectors were linearized in the AOX1 promoter (with Pmel) before transformation to *P. pastoris* to promote homologous recombination in the endogenous AOX1 locus for stable integration into the genome. The resulting vectors were named pKai-DS-Cav1-4, pKai-DS-Cav1-L66, pKai-VHH-F2 and pKai-VHH-F58 and used to transform *Pichia pastoris* strain GS115 using the condensed transformation protocol described by Lin-Cereghino et al., 2005.

Purification of VHHs Produced by *Pichia pastoris*

Expression of VHH by transformed *Pichia pastoris* clones was first analysed in 2 ml cultures. On day one individual transformants were used to inoculate 2 ml of YPNG medium (2% pepton, 1% Bacto yeast extract, 1.34% YNB, 0.1M potassium phosphate pH6, 0.00004% biotine, 1% glycerol) with 100 μg/ml Zeocin (Life Technologies) and incubated while shaking at 28° C. for 24 h. The next day, cells were pelleted by centrifugation (8 minutes at 500 g) and the YPNG medium was replaced by YPNM medium (2% pepton, 1% Bacto yeast extract, 1.34% YNB, 0.1M potassium phosphate pH6, 0.00004% biotine, 1% methanol) to induce VHH expression and cultures were incubated at 28° c. while shaking for 72 h. Fifty 50 μl of 50% methanol was added to the cultures at 72 h, 80 h and 96 h. One hundred h after transfer to methanol containing medium the yeast cells were pelleted by centrifugation (8 minutes at 500 g) and the supernatant was retained to assess the presence of VHH. Crude medium (25 μl) was loaded on a 15% SDS-PAGE gel, after which presence of protein was analysed by Coomassie Brilliant Blue staining. To select VHHs with RSV neutralizing activity, we determined such activity in the crude YPNM supernatant from individual *Pichia pastoris* transformants by applying serial dilutions of the supernatant in a plaque assay as described above.

*Pichia pastoris* transformants that yielded high levels of VHH in the medium or with high RSV neutralizing activity were selected for scale up using 100 or 300 ml *Pichia* cultures. Growth and methanol induction conditions, and harvesting of medium were similar as mentioned above for the 2 ml cultures. The cleared medium was subjected to ammonium sulphate precipitation (80% saturation) for four hours at 4° C. The insoluble fraction was pelleted by centrifugation at 20,000 g and solubilized in 10 ml HisTrap binding buffer (20 mM sodium phosphate, 0.5 M NaCl, 20 mM imidazole, pH 7.4), centrifuged for 10 minutes at 4° C. after which the supernatant was loaded on a 1 ml HisTrap HP column (GE Healthcare), pre-equilibrated with the HisTrap binding buffer. After washing the column with at least 10 column volumes of HisTrap binding buffer (until the absorbance reaches a steady baseline), the bound proteins were eluted with a linear imidazole gradient starting from 20 mM and ending at 500 mM imidazole in HisTrap binding buffer over a total volume of 20 ml. Fractions containing the VHH, as determined by SDS-PAGE analysis were pooled, and concentrated to 2 ml with a Vivaspin column (5 kDa cutoff, GE Healthcare). These concentrated fractions were then loaded on a Superdex 75 column (160 ml, 0.8 ml/min) in PBS and peak fractions were pooled and concentrated on a Vivaspin column with a 5 kDa cutoff. The protein concentration of the pooled fraction was determined by A280 measurement by NanoDrop 1000 with the percent solution extinction coefficient customized to each VHH. The pooled and concentrated fractions were aliquoted and stored at −80° C. before further use.

Calculation of 50% Inhibitory Concentration (IC50) of Purified VHHs

To determine the IC50 of the purified VHHs produced by *Pichia pastoris* threefold serial dilutions prepared in Opti-Mem of these VHHs were evaluated in an RSV neutralization assay as described above. Monoclonal IgGs D25 and AM22 (Beaumont et al., 2012, Spits et al., 2013), both specifically directed at the prefusion conformation of F, were used as positive controls. NB 1.12, a VHH directed against α-macroglobulin was used as a negative control. IC50 values were calculated manually.

In Vitro Binding of VHHs to DS-Cav1 and Postfusion F

The binding of the purified VHHs to DS-Cav1 and postfusion F was tested in a direct ELISA. Microtiter plates (type II, F96 Maxisorp, Nunc) were coated with 100 μl of a 1 μg/ml DS-Cav1 solution or a 1 μg/ml postfusion F solution in PBS. After washing, the plates were blocked for one h with 200 μl of 4% milk in PBS after which they were washed again with PBS once. A 1/3 dilution series of the VHHs (starting from 30 μg/ml) was then applied to the protein-coated wells. After one hour, the plates were washed and a 1/2000 dilution of anti-Histidine Tag antibody (AD1.1.10 AbD Serotec) in PBS was added for an hour. After washing and addition of HRP-linked anti-mouse IgG during one h (in a 1/2000 dilution), the ELISA was developed in the same way as the PE-ELISA described above. For affinity determination, purified DS-Cav1 with a StrepTag II and a 6×HisTag was captured on an NTA sensor chip to approximately 537 response units (RU) for each cycle using a Biacore X100 (GE). The NTA sensor chip was regenerated between cycles using 0.25M EDTA followed by 0.5 mM NiCl2. A buffer-only sample was injected over the DS-Cav1 and reference flow cells, followed by Nb4 or Nb66 2-fold serially diluted from 5 nM to 39.1 pM in HBS-P+, with a duplication of the 1.25 nM concentration. The data were double-reference subtracted and fit to a 1:1 binding model using Scrubber.

Binding of the VHHs to F expressed on the surface of cells that had been transfected with an RSV F cDNA expression vector was evaluated by flow cytometry. HEK293T cells were seeded at 4,000,000 cells per 150 mm tissue culture plate and transfected with 6.4 μg pCAGGS-Fsyn, which encodes a codon-optimized RSV F cDNA, with the FuGENE HD transfection reagent (Promega). To trace transfected cells, transfections were performed in the presence of 6.4 μg of peGFP-NLS. Control transfections were performed with peGFP-NLS only. Eighteen h after transfection the cells were detached with 15 ml trypsin-EDTA solution (0.05% trypsin, 0.5 mM EDTA (pH 8.0)) washed once in PBS and incubated for 30 minutes in PBS containing 1% BSA (PBS/BSA). Subsequently the cells were incubated with the indicated VHH or with RSV-F specific mouse monoclonal antibody (MAB858-1, Chemicon International) at different concentrations as indicated in FIG. 8). One h later the cells were washed once with PBS/BSA and incubated with anti-Histidine Tag antibody diluted 1/3000 in PBS/BSA during one h. Next, the cells were washed once with PBS/BSA and anti-mouse IgG Alexa 633 was added during 30 minutes. After washing the cells three times with PBS, the cells were analyzed using a FACSCalibur flow cytometer. Single GFP expressing cells were selected based on the peak surface of the sideward scatter signal, the peak surface and peak height of the forward scatter signal and the peak surface of the green fluorescence signal. Finally, of these GFP positive single cells, the Alexa 633 fluorescence intensity signal was measured.

Mice

Specific pathogen-free, female BALB/c mice were obtained from Charles River (Charles River Wiga, Sulzfeld, Germany). The animals were housed in a temperature-controlled environment with 12 h light/dark cycles; food and water were provided ad libitum. The animal facility operates under the Flemish Government License Number LA1400536. All experiments were done under conditions specified by law and authorized by the Institutional Ethical Committee on Experimental Animals (Ethical application EC2015-019).

Administration of VHHs and Monoclonal Antibodies and RSV Challenge of Mice

Mice were slightly anesthesized by isoflurane before intranasal administration of VHH, palivizumab or RSV challenge virus. VHH, palivizumab (Synagis, Medimmune) and RSV virus were administered in a total volume of 50 μl formulated in PBS, which was distributed equally over the two nostrils. Each group of five mice received 30 μg of DS-Cav1-4, 30 μg of VHH DS-Cav1-L66, 30 μg of VHH-F2 (as a negative control) or 30 μg of palivizumab (as a positive control) four hours before infection with 1,000,000 PFU of RSV A2. All groups also received 30 μg of the negative control VHH-F2 24h after infection.

Determination of Lung Viral Titers by Plaque Assay

Five days after challenge, the mice were sacrificed by cervical dislocation. The mouse lungs were removed aseptically and homogenized by vigorous shaking with a Mixer Mill MM 2000 (Retsch) in the presence of a sterile metal bead in 1 ml HBSS containing 20% sucrose and supplemented with 1% penicillin and 1% streptomycin. Lung homogenates were subsequently cleared by centrifugation (10 minutes at 2500 rpm) at 4° C. and used in duplicate for virus titration on Vero cells. Monolayers of Vero cells were infected with 50 μl of serial 1:3 dilutions of lung homogenates in a 96-well plate in serum-free Opti-MEM medium (Invitrogen) supplemented with penicillin and streptomycin. The plaque assay was further processed as described above. The plaques in each well were counted and for each dilution the number of PFU per lung (1 ml) was calculated as follows: number of plaques present in the dilution×the dilution×20 (=1000 μl total supernatant volume/50 μl of supernatant used to infect the first well of the dilution series). The number of PFU in each lung was than calculated as the average of the duplicates.

Determination of Lung Viral Titer by qRT-PCR

To determine the lung RSV load by qRT-PCR, total RNA from the cleared lung homogenates was prepared by using the High Pure RNA tissue Kit (Roche, Mannheim) according to the manufacturer's instructions. cDNA was prepared by the use of random hexamer primers and the Transcriptor First strand cDNA synthesis kit (Roche, Mannheim). The relative levels of genomic RSV M cDNA were determined by qRT-PCR using primers specific for the RSV A2 M gene (5'TCACGAAGGCTCCACATACA3' SEQ ID NO: 14) and 5'GCAGGGTCATCGTCTTTTTC3' (SEQ ID NO: 15)) and a nucleotide probe (#150 Universal Probe Library, Roche) labeled with fluorescein (FAM) at the 5'-end and with a dark quencher dye near the 3'-end. The qRT-PCR data were normalized to mRPL13A mRNA levels present in the samples of each mouse.

Antibody Cross-Competition on DS-Cav1-Binding

DS-Cav1 protein (10 μg/ml) was immobilized on AR2G biosensors through amine coupling reaction in acetate buffer (pH 5.0). The reaction was quenched by 1M ethanolamine and DS-Cav1-immobilized biosensors were then equilibrated with assay buffer (PBS with 1% BSA). The biosensors were dipped in competitor antibodies (35 μg/ml in assay buffer) followed by analyte antibodies (35 μg/ml in assay buffer) with a short baseline step in between two antibody steps.

Example 1: RSV Neutralizing Activity in Llama Plasma

To assess the induction of humoral anti-RSV responses in the llama after immunization with DS-Cav1, plasma samples obtained before and after each immunization were tested in a RSV-neutralization assay. The samples were tested for their neutralizing activity against RSV-A2 and a clinical strain of RSV B, RSV B49. FIG. 1 illustrates that all plasma samples obtained after the fourth immunization have high neutralizing activity against RSV A2 and RSV B49.

Example 2: Isolation of DS-Cav1-Specific VHHs

The VHH phage library was subjected to one round of panning on the DS-Cav1 protein. The enrichment for DS-Cav1-specific phages was assessed by comparing the number of phages eluted from DS-Cav1-coated wells with the number of phages eluted from the uncoated wells. The number of eluted phages was estimated indirectly by determining the ampicillin resistance transducing units, i.e. the number of TG1 colonies that had been transduced with the phages eluted in the panning step. This experiment suggested that the phage population was enriched about 140-fold for DS-Cav1-specific phages. Ninety colonies were randomly selected and analyzed by ELISA for the presence of VHHs specific for the prefusion conformation of F (DS-Cav1) versus the postfusion conformation of F in their periplasmic extracts. The result of this ELISA is depicted in FIG. 2. Out of the 90 colonies, 37 colonies scored positive (10 scored positive for binding to both pre- and postfusion F, 19 scored positive for binding to only prefusion F and 8 scored positive for binding to only postfusion F). The VHH sequence of all colonies that suggested binding to pre- and or postfusion F was determined. Twenty eight clones out of 37 had a unique VHH sequence and were selected for further use. The VHH sequences of these clones were cloned into a *Pichia pastoris* expression vector and the resulting plasmids were subsequently used to transform *Pichia pastoris.*

Example 3: Testing Neutralizing Activity in *Pichia pastoris* Supernatants

Figure 3:
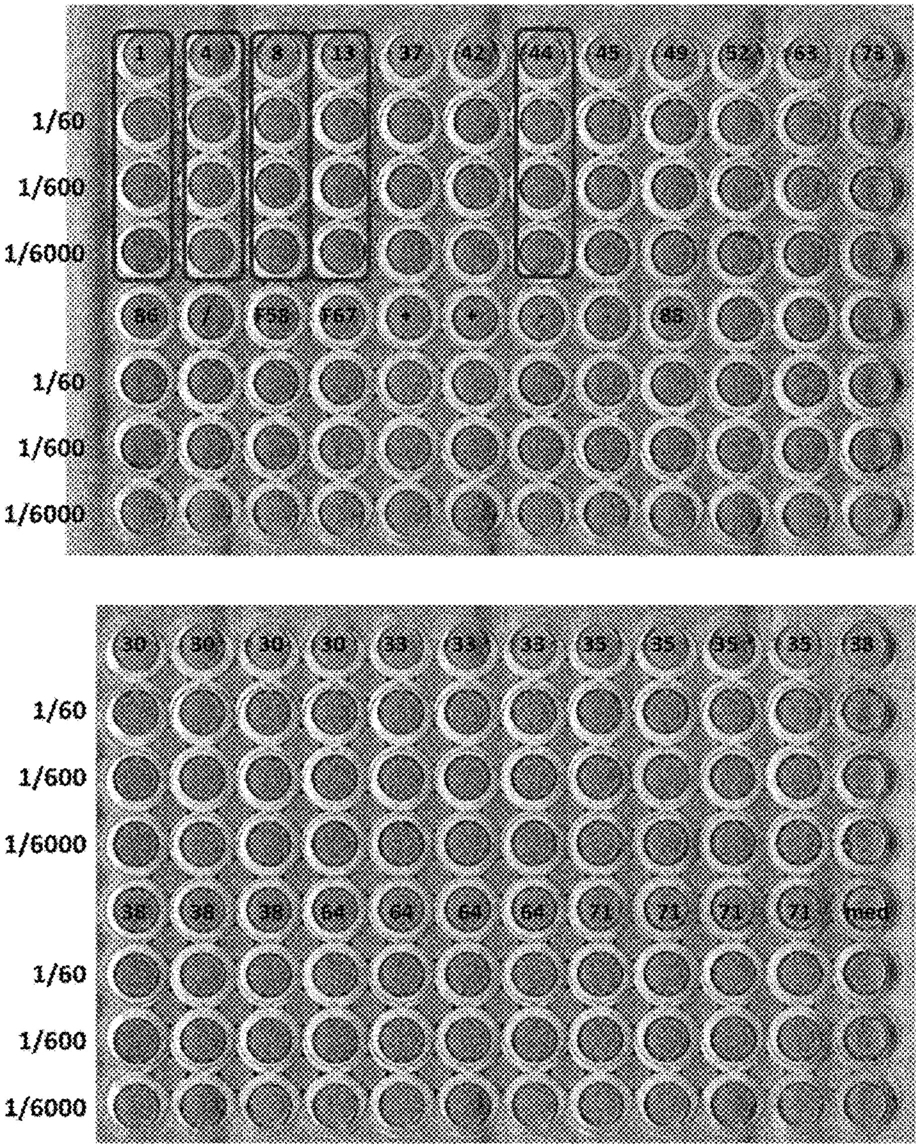
FIG. 3: Detection of RSV neutralizing activity in *Pichia pastoris* supernatants. pKai61-VHH *P. pastoris* transformants were pre-cultured in 2 ml YPNG medium in a 24-well format for 24 hours. Subsequently, the cells were placed in YPNM medium for 48 hours to induce VHH expression. 1/60, 1/600 and 1/6000 dilutions of the cleared culture supernatant were tested for neutralizing activity by mixing with RSV A2 (30 PFU/well), which was used to inoculate a monolayer of Vero cells. Boxes indicate *P. pastoris* clones with neutralizing activity. (A) *P. pastoris* clones obtained after transformation with a select set of unique pKai61-VHH plasmids, referred to by the numbers. (B) *P. pastoris* clones obtained after transformation with pKai61 in which a library of candidate F-specific VHHs was cloned. L3, L13, etc. refer to individual *P. pastoris* transformants. Boxed wells indicate samples with RSV-neutralizing activity.
Figure 3:
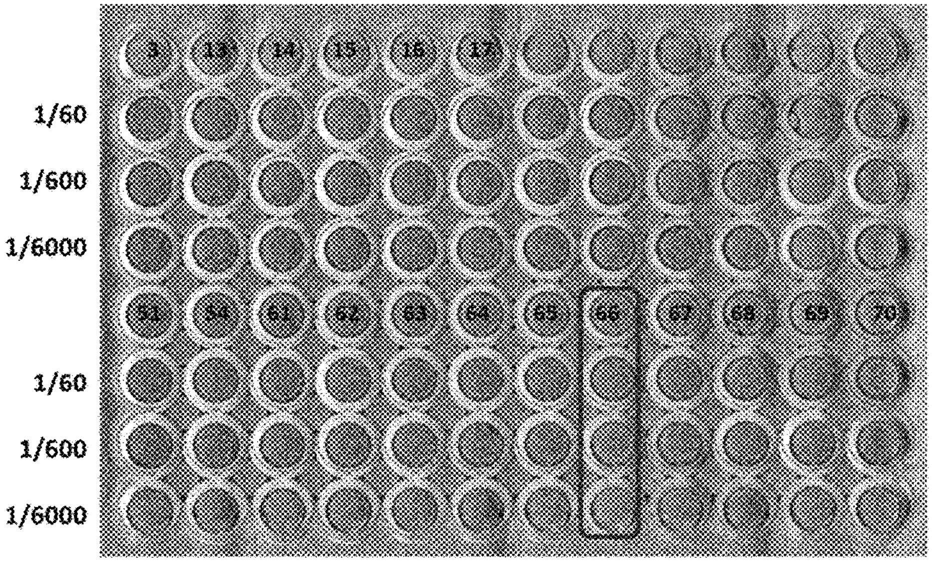

We also attempted to clone the VHH cDNA library obtained after one round of panning on DS-Cav1 into the *Pichia pastoris* expression vector pKai61. We used this strategy in order to try to select biologically relevant VHH candidates based on RSV neutralizing activity in the supernatant of individual *Pichia pastoris* transformants. From the 20 individual *Pichia pastoris* transformants selected based on binding to F, five had neutralizing activity against RSV A2 (with DS-Cav1-4 being the most potent one), while from 18 clones obtained from the library cloning into pKai61, only one (VHH DS-Cav1-L66) displayed neutralizing activity (FIG. 3).

The cDNA sequence of DS-Cav1-4 and DS-Cav1-L66 was determined by Sanger sequencing and the nucleotide sequence as well as the deduced amino acid sequence are shown in FIG. 5.

Example 4: Production and Determination of IC50 of Purified VHHs

Figure 4:
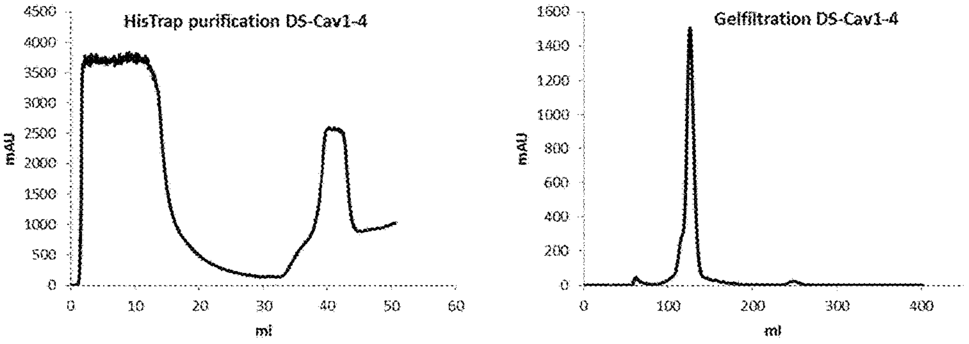
FIG. 4: Purification of VHHs produced in *Pichia pastoris*. The culture medium of *P. pastoris* cells that had been transformed with pKai-VHH-DS-Cav1-4, pKai-VHH-DS-Cav1-L66, pKai-VHH-F2 or pKai-VHH-F58 was harvested after induction with methanol for 96 h. Resolubilized ammonium sulphate precipitate of the cell-free medium was loaded onto a HisTrap column and after washing the column was eluted with an increasing concentration gradient of imidazole (left). The peak fraction that eluted from the HisTrap column was subsequently loaded on a Superdex 75 gelfiltration column (right). The chromatographs are shown for VHH-DS-Cav1-4 (A), VHH-DS-Cav1-L66 (B), VHH-F2 (C) and VHH-F58 (D).

Prior to purification, VHH DS-Cav1-4 and VHH DS-Cav1-L66 had the most potent RSV neutralizing VHHs and these two VHHs as well as negative control VHHs F2 and F58 were produced in 300 ml *Pichia pastoris* cultures and purified by HisTrap purification followed by superdex 75 size exclusion chromatography (FIG. 4). VHH F2 and VHH F58 are irrelevant control VHHs obtained from a VHH library derived from a different llama that had been immunized with inactived Junin virus. VHH DS-Cav1-4 and VHH DS-Cav1-L66 in vitro neutralized RSV A2 with an IC50 of 0.021 nM and 0.032 nM, respectively. For neutralization of RSV B49 VHH DS-Cav1-4 and VHH DS-Cav1-L66 displayed an IC50 of 0.015 nM and 0.032 nM, respectively. To evaluate if VHH DS-Cav1-4 and VHH DS-Cav1-L66 could neutralize human Metapneumovirus A and/or B serotypes, pre-determined amounts of GFP-expressing hMPV recombinant viruses (NL/1/00 A1 sublineage or NL/1/99 B1 sublineage, a kind gift of Bernadette van den Hoogen and Ron Fouchier, Rotterdam, the Netherlands) or GFP-hRSV (A2 strain, a kind gift of Mark Peeples, Columbus, Ohio, USA) (MOI 0.3 ffu/cell) were mixed with serial dilutions of VHHs or mAbs and added to cultures of either Vero-118 (hMPV) or HEp-2 cells, growing in 96-well plates. Thirty-six hours later, the medium was removed, PBS was added and the fluorescent intensity of GFP per well was measured with a Tecan microplate reader M200. Fluorescence values were plotted as percent of a virus control without antibody and used to calculate the corresponding IC50 values.

Example 5: DS-Cav1-4 and DS-Cav1-166 Bind to RSV F in the Prefusion State but not to RSV F in the Postfusion State To evaluate the binding ability of DS-Cav1-4 and DS-Cav1-L66 to pre- and postfusion F, we performed an ELISA in which F in either conformation was coated directly on the microtiter plate and a threefold dilution series of VHHs was added to this plate (FIG. 7A). We found that VHH DS-Cav1-4 and VHH DS-Cav1-L66 bound specifically to coated prefusion F and not to coated F in the postfusion conformation. To further characterize the binding affinity to prefusion F protein, we performed SPR-based binding experiments. We found that both ISVDs bind to prefusion RSV F with a picomolar affinity. It is surprising that the ISVDs display such a high affinity for its target, as they are monovalent, contrary to conventional monoclonal antibodies such as palivizumab or AM14 (Gilman et al., 2015) that are bivalent by nature. In particular, the off-rate of DS-Cav1-4 is very low.

Binding of VHH DS-Cav1-4 and VHH DS-Cav1-L66 to F expressed by mammalian cells was also evaluated. HEK293T cells were co-transfected with pCAGGS-Fsyn, encoding a codon optimized F cDNA and peGFP-NLS. Cells were harvested 18 h after transfection and stained with VHH DS-Cav1-4, VHH DS-Cav1-L66, negative control VHHs F58 and F2 and a monoclonal mouse IgG antibody specific for RSV-F. Binding of the VHHs to the GFP positive cells in the co-transfection setting was compared with binding to GFP positive cells that had been transfected with the GFP expression vector only. Clear binding was observed for all dilutions of VHH DS-Cav1-4 and VHH DS-Cav1-L66 and for the three highest concentrations of the positive control monoclonal antibody directed against RSV F (FIG. 8).

Example 6: DS-Cav1-4 and DS-Cav1-166 Bind to a New Epitope of RSV F

To investigate whether DS-Cav1-4 and DS-Cav1-L66 bind to the recently described prefusion F specific epitope ø, we investigated if these VHHs can compete with the epitope ø specific D25 antibody for the binding to the RSV prefusion F protein by biolayer interferometry (FIG. 9). The competition assay illustrates that neither VHH competes with D25. In contrast, both VHHs did compete with each other. These results indicate that both VHHs bind to overlapping epitopes, but those epitopes are different from the D25 epitope ø.

Figure 13:
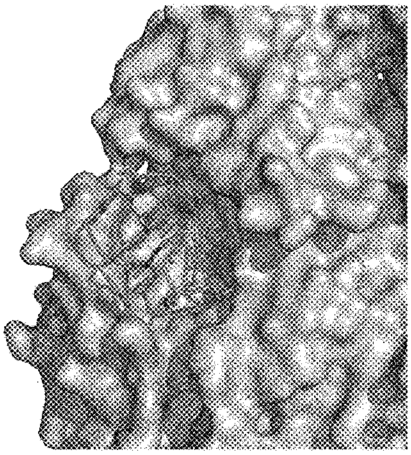
FIG. 13: Binding specifics of VHH-DS-Cav1-166. (A) CDR3 loop of VHH-DS-Cav1-L66 binds to a pocket formed by two protomers of RSV F. (B) CDR2 loop of VHH-DS-Cav1-L66 interacts with site II and is joined to CDR3 through a disulfide bond. P1=protomer 1; P2=protomer 2.
Figure 13:
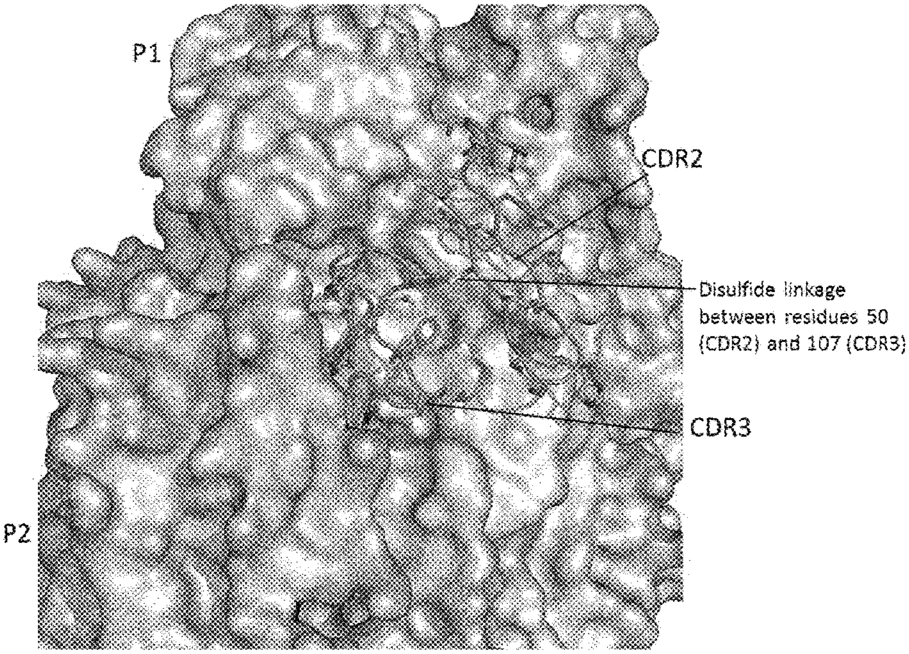

Further characterization of the ISVD epitopes confirmed that DS-Cav1-4 and DS-Cav1-L66 bind the same epitope on RSV F, with high structural conservation (FIG. 11A-D). In FIG. 11C the residues of prefusion-stabilized RSV F protein (full open reading frame, before in vivo processing, SEQ ID NO: 17) that are contacted by both, DS-Cav1-4 and DS-Cav1-L66 are underlined. In particular, the following amino acid residues of the RSV F protein form part of the epitope of DS-Cav1-4 and DS-Cav1-L66: T50, G51, W52, S180, G184, V185, P265, I266, T267, N268, D269, Q270, L305, G307, V308, N345, A346, G347, K421, S425, K427, N428, R429, G430, I431, S451, G453, N454, L456, Y458. These residues represent the epitope of both DS-Cav1-4 and DS-Cav1-L66. Further details of the binding of the CDR2 and CDR3 loops are shown in FIG. 12 (for DS-Cav1-4) and FIG. 13 (for DS-Cav1-L66).

Figure 14:
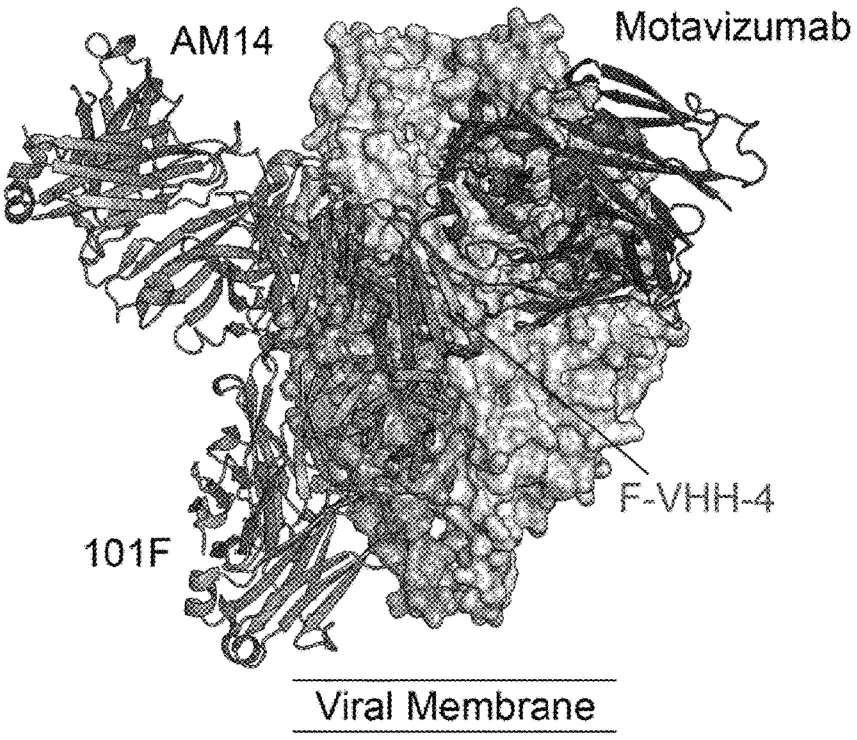
FIG. 14. Structure of the F protein in prefusion conformation in complex with motavizumab, AM14, 101F and DS-Cav1-4. Model of the F protein in prefusion conformation in complex with motavizumab, AM14, 101F and DS-Cav1-4. The AM14-Mota-prefusion F structure (4ZYP) and the peptide bound 101F Fab structure (3O41) were aligned to F of the DS-Cav1-4 bound prefusion F structure. The epitope of DS-Cav1-4, as well as that of DS-Cav1-L66, is located between those of AM14, motavizumab and 101F and partially overlaps with each of these.

The structure of the F protein in prefusion conformation in complex with motavizumab, AM14, 101F and DS-Cav1-4 revealed a new binding epitope (FIG. 14). All other antibodies for which the co-crystal structure with RSV F is known bind to an epitope that is different from that bound by DS-Cav1-4 and DS-Cav1-L66. Even the antibodies that compete for binding to prefusion-stabilized RSV F with DS-Cav1-4 (i.e. AM14 and palivizumab) and DS-Cav1-L66 (i.e. AM14, palivizumab and 101F) and for which the binding epitope has been unequivocally determined by co-crystal structure analysis, bind to a different epitope in RSV F. This is shown in FIG. 14. We note that palivizumab and motavizumab bind the same epitope in RSV F and that this epitope is present in the prefusion and postfusion state of RSV F.

Example 7: Testing Prophylactic Anti-RSV Activity of VHHs In Vivo

To test if prophylactic administration of VHH DS-Cav1-4 or DS-Cav1-L66 can protect against RSV challenge in vivo, female BALB/c mice (five mice per group) received 30 μg of VHH DS-Cav1-4, VHH DS-Cav1-L66, F2 VHH or palivizumab intranasally four h before infection with 1.106 PFU of RSV A2). Twenty four h after challenge, all mice received 30 μg of F2 VHH intranasally. Five days after challenge, the mice were sacrificed and lungs were homogenized in 1 ml of HBSS supplemented with 20% sucrose, penicillin and streptomycin. Mice that had been treated with DS-Cav1-4, DS-Cav1-L66 or palivizumab had no detectable replicating virus in their lungs (except one mouse treated with palivizumab) (FIG. 10 A) in contrast to the group which had been treated with the F2 VHH which displayed high levels of replicating virus in their lungs (about 1×105 PFU). As plaque assays used to quantify the level of replicating virus in the lungs can be affected by the presence of neutralizing antibodies or VHHs, we additionally quantified the level of RSV RNA in the lung homogenates by qRT-PCR. Mice that had been treated with DS-Cav1-4 and DS-Cav1-L66 displayed on average more than 3000 times less viral RNA as compared to the F2 treated control mice. Mice that had been treated with palivizumab displayed on average about 100 fold less viral RNA as compared to the F2 treated control mice.

REFERENCES

1. Gilman, M. S. A., et al. Characterization of a prefusion-specific antibody that recognizes a quaternary, cleavage-dependent epitope on the RSV fusion glycoprotein. *PLoS Pathog,* 11, 1-17 (2015).
2. Hultberg, A., et al. Llama-derived single domain antibodies to build multivalent, superpotent and broadened neutralizing anti-viral molecules. *PLoS One,* 6, e17665 (2011).
3. Lin-Cereghino, J., et al. Condensed protocol for competent cell preparation and transformation of the methylotrophic yeast *Pichia pastoris. Biotechniques,* 38, 44, 46, 48 (2005).
4. McLellan, J. S., et al. Structure of respiratory syncytial virus fusion glycoprotein in the postfusion conformation reveals preservation of neutralizing epitopes. *J Virol,* 85, 7788-96 (2011).
5. McLellan, J. S., et al. Structure of RSV fusion glycoprotein trimer bound to a prefusion-specific neutralizing antibody. *Science* 340, 1113-1117 (2013).
6. McLellan, J. S., et al. Structure-based design of a fusion glycoprotein vaccine for respiratory syncytial virus. *Science* 342, 592-598 (2013).
7. Scheppens, B., et al. Nanobodies specific for respiratory syncytial virus fusion protein protect against infection by inhibition of fusion. *J. Infect Dis.,* 11, 1692-701(2011).
8. Schoonooghe, S., et al. Efficient production of human bivalent and trivalent anti-MUC1 Fab-scFv antibodies in *Pichia pastoris. BMC Biotechnol.,* 9, 70 (2009).
9. Tan, L., et al. The comparative genomics of human respiratory syncytial virus subgroups A and B: genetic variability and molecular evolutionary dynamics. *J Virol.* 87, 8213-26 (2013).

The invention claimed is:

1. An immunoglobulin single variable domain (ISVD) that binds specifically to the prefusion form of the fusion (F) protein of respiratory syncytial virus (RSV), characterized in that the ISVD shows in monovalent format a neutralization activity of RSV serotypes A and B for which the $IC_{50}$ value differs ten-fold or less, and in that the ISVD binds to a conformational epitope of RSV prefusion F protein comprising amino acids 50-52, 180, 184, 185, 265-270, 305, 307, 308, 345-347, 421, 425, 427-431, 451, 453, 454, 456 and 458 as depicted in SEQ ID NO: 17, characterized in that said ISVD comprises CDR1 sequence SEQ ID NO: 1, a CDR2 sequence selected from the group consisting of SEQ ID NO: 3 and SEQ ID NO: 4, and a CDR3 sequence selected from the group consisting of SEQ ID NO: 5 and SEQ ID NO: 6.

2. A RSV binding construct, characterized in that said RSV binding construct comprises the ISVD according to claim 1.

3. A purified nucleic acid, characterized in that said nucleic acid encodes the ISVD according to claim 1.

4. A cultured host cell, characterized in that said host cell is transformed or transfected with the nucleic acid according to claim 3.

5. A method of producing an ISVD comprising culturing the host cell according to claim 4.

6. A method of inhibiting RSV infection in a subject comprising administering the ISVD according to claim 1.

7. A method of inhibiting RSV infection in a subject comprising administering the ISVD according to claim 1, wherein the ISVD is administered prophylactically.

8. A pharmaceutical composition, characterized in that said pharmaceutical composition comprises at least one ISVD according to claim 1.

9. A method of inhibiting RSV infection in a subject comprising administering the pharmaceutical composition according to claim 8.

10. A method of inhibiting RSV infection in a subject comprising administering the pharmaceutical composition according to claim 8, wherein the pharmaceutical composition is administered prophylactically.

11. A method of inhibiting RSV infection in a subject comprising administering the RSV binding construct according to claim 2.

12. A method of inhibiting RSV infection in a subject comprising administering the RSV binding construct according to claim 2, wherein the RSV binding construct is administered prophylactically.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: CDR1 sequence

<400> SEQUENCE: 1

Gly Phe Thr Leu Asp Tyr Tyr Tyr Ile Gly
1               5                   10


<210> SEQ ID NO 2
<211> LENGTH: 10
<212> TYPE: PRT
<213> ORGANISM: Artificial Sequence
<220> FEATURE:
<223> OTHER INFORMATION: CDR1 sequence

<400> SEQUENCE: 2

Gly Phe Thr Leu Asp Tyr Tyr Tyr Ile Gly
1               5                   10


<210> SEQ ID NO 3
<211> LENGTH: 17
<212> TYPE: PRT
<213> ORGANISM: Artificial Sequence
<220> FEATURE:
<223> OTHER INFORMATION: CDR2 sequence

<400> SEQUENCE: 3

Cys Ile Ser Gly Ser Ser Gly Ser Thr Tyr Tyr Pro Asp Ser Val Lys
1               5                   10                  15

Gly


<210> SEQ ID NO 4
```

```
<211> LENGTH: 17
<212> TYPE: PRT
<213> ORGANISM: Artificial Sequence
<220> FEATURE:
<223> OTHER INFORMATION: CDR2 sequence

<400> SEQUENCE: 4

Cys Ile Ser Ser Ser His Gly Ser Thr Tyr Tyr Ala Asp Ser Val Lys
1               5                   10                  15

Gly


<210> SEQ ID NO 5
<211> LENGTH: 16
<212> TYPE: PRT
<213> ORGANISM: Artificial Sequence
<220> FEATURE:
<223> OTHER INFORMATION: CDR3 sequence

<400> SEQUENCE: 5

Ile Arg Ser Ser Ser Trp Gly Gly Cys Val His Tyr Gly Met Asp Tyr
1               5                   10                  15


<210> SEQ ID NO 6
<211> LENGTH: 16
<212> TYPE: PRT
<213> ORGANISM: Artificial Sequence
<220> FEATURE:
<223> OTHER INFORMATION: CDR3 sequence

<400> SEQUENCE: 6

Val Ala Val Ala His Phe Arg Gly Cys Gly Val Asp Gly Met Asp Tyr
1               5                   10                  15


<210> SEQ ID NO 7
<211> LENGTH: 396
<212> TYPE: DNA
<213> ORGANISM: Artificial Sequence
<220> FEATURE:
<223> OTHER INFORMATION: single domain antibody DS-Cav1-4
<220> FEATURE:
<221> NAME/KEY: CDS
<222> LOCATION: (1)..(396)

<400> SEQUENCE: 7

cag gtg cag ctg cag gag tct ggg gga ggc ttg gtg cag cct ggg ggg       48
Gln Val Gln Leu Gln Glu Ser Gly Gly Gly Leu Val Gln Pro Gly Gly
1               5                   10                  15

tct ctg aga ctc tcc tgt gca gcc tct gga ttc act ttg gat tat tat       96
Ser Leu Arg Leu Ser Cys Ala Ala Ser Gly Phe Thr Leu Asp Tyr Tyr
            20                  25                  30

tac ata ggc tgg ttc cgc cag gcc cca ggg aag gag cgc gag gca gtc      144
Tyr Ile Gly Trp Phe Arg Gln Ala Pro Gly Lys Glu Arg Glu Ala Val
        35                  40                  45

tca tgt att agt ggt agt agt ggt agc aca tac tat cca gac tcc gtg      192
Ser Cys Ile Ser Gly Ser Ser Gly Ser Thr Tyr Tyr Pro Asp Ser Val
    50                  55                  60

aag ggc cga ttc acc atc tcc aga gac aat gcc aag aac acg gtg tat      240
Lys Gly Arg Phe Thr Ile Ser Arg Asp Asn Ala Lys Asn Thr Val Tyr
65                  70                  75                  80

ctg caa atg aac agc ctg aaa cct gag gac acg gcc gtt tat tac tgt      288
Leu Gln Met Asn Ser Leu Lys Pro Glu Asp Thr Ala Val Tyr Tyr Cys
                85                  90                  95

gcg aca att cgt agt agt agc tgg ggg ggt tgc gtg cac tac ggc atg      336
Ala Thr Ile Arg Ser Ser Ser Trp Gly Gly Cys Val His Tyr Gly Met
            100                 105                 110
```

-continued

```
gac tac tgg ggc aaa ggg acc cag gtc acc gtc tcc agc cac cac cat      384
Asp Tyr Trp Gly Lys Gly Thr Gln Val Thr Val Ser Ser His His His
        115                 120                 125

cac cat cac tag                                                      396
His His His
    130


<210> SEQ ID NO 8
<211> LENGTH: 131
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Ala Val
        35                  40                  45

Ser Cys Ile Ser Gly Ser Ser Gly Ser Thr Tyr Tyr Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Ile Arg Ser Ser Ser Trp Gly Gly Cys Val His Tyr Gly Met
            100                 105                 110

Asp Tyr Trp Gly Lys Gly Thr Gln Val Thr Val Ser Ser His His His
        115                 120                 125

His His His
    130


<210> SEQ ID NO 9
<211> LENGTH: 396
<212> TYPE: DNA
<213> ORGANISM: Artificial Sequence
<220> FEATURE:
<223> OTHER INFORMATION: Single domain antibody DS-Cav1-L66
<220> FEATURE:
<221> NAME/KEY: CDS
<222> LOCATION: (1)..(396)

<400> SEQUENCE: 9

cag gtg cag ctg cag gag tct ggg gga ggc ttg gtg cag cct ggg ggg       48
Gln Val Gln Leu Gln Glu Ser Gly Gly Gly Leu Val Gln Pro Gly Gly
1               5                   10                  15

tct ctg aga ctc tcc tgt gca gcc tct gga ttc act ttg gat tat tat       96
Ser Leu Arg Leu Ser Cys Ala Ala Ser Gly Phe Thr Leu Asp Tyr Tyr
            20                  25                  30

tac ata ggc tgg ttc cgc cag gcc cca ggg aag gag cgc gag ggg gtc      144
Tyr Ile Gly Trp Phe Arg Gln Ala Pro Gly Lys Glu Arg Glu Gly Val
        35                  40                  45

tca tgt att agt agt agt cat ggt agc aca tac tat gca gac tcc gtg      192
Ser Cys Ile Ser Ser Ser His Gly Ser Thr Tyr Tyr Ala Asp Ser Val
    50                  55                  60

aag ggc cga ttc acc atc tcc aga gac aat gcc aag aac acg gtg tat      240
Lys Gly Arg Phe Thr Ile Ser Arg Asp Asn Ala Lys Asn Thr Val Tyr
65                  70                  75                  80
```

-continued

```
ctg cag atg aac agc ctg aaa cct gag gac acg gcc gtt tat tac tgt      288
Leu Gln Met Asn Ser Leu Lys Pro Glu Asp Thr Ala Val Tyr Tyr Cys
                85                  90                  95

gcg aca gta gct gta gca cat ttc cgg ggt tgc gga gtc gac ggc atg      336
Ala Thr Val Ala Val Ala His Phe Arg Gly Cys Gly Val Asp Gly Met
            100                 105                 110

gac tac tgg ggc aaa ggg acc cag gtc acc gtc tcc agc cac cac cat      384
Asp Tyr Trp Gly Lys Gly Thr Gln Val Thr Val Ser Ser His His His
        115                 120                 125

cac cat cac tag                                                      396
His His His
    130
```

```
<210> SEQ ID NO 10
<211> LENGTH: 131
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Gly Val
        35                  40                  45

Ser Cys Ile Ser Ser Ser His Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Val Ala Val Ala His Phe Arg Gly Cys Gly Val Asp Gly Met
            100                 105                 110

Asp Tyr Trp Gly Lys Gly Thr Gln Val Thr Val Ser Ser His His His
        115                 120                 125

His His His
    130
```

```
<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11

caggaaacag ctatgacc                                                   18
```

```
<210> SEQ ID NO 12
<211> LENGTH: 47
<212> TYPE: DNA
<213> ORGANISM: Artificial Sequence
<220> FEATURE:
<223> OTHER INFORMATION: Primer

<400> SEQUENCE: 12

ggcgggtatc tctcgagaaa aggcaggtgc agctgcagga gtctggg                   47
```

```
<210> SEQ ID NO 13
```

-continued

<211> LENGTH: 49
<212> TYPE: DNA
<213> ORGANISM: Artificial Sequence
<220> FEATURE:
<223> OTHER INFORMATION: Primer

<400> SEQUENCE: 13
ctaactagtc tagtgatggt gatggtggtg gctggagacg gtgacctgg 49

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcacgaaggc tccacataca 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcagggtcat cgtctttttc 20

<210> SEQ ID NO 16
<211> LENGTH: 461
<212> TYPE: PRT
<213> ORGANISM: Artificial Sequence
<220> FEATURE:
<223> OTHER INFORMATION: prefusion-stabilized RSV F protein (figure 11a+b)

<400> SEQUENCE: 16

```
Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Phe Leu Gly Phe Leu Leu Gly Val Gly Ser Ala Ile
                85                  90                  95

Ala Ser Gly Val Ala Val Cys Lys Val Leu His Leu Glu Gly Glu Val
            100                 105                 110

Asn Lys Ile Lys Ser Ala Leu Leu Ser Thr Asn Lys Ala Val Val Ser
        115                 120                 125

Leu Ser Asn Gly Val Ser Val Leu Thr Phe Lys Val Leu Asp Leu Lys
    130                 135                 140

Asn Tyr Ile Asp Lys Gln Leu Leu Pro Ile Leu Asn Lys Gln Ser Cys
145                 150                 155                 160

Ser Ile Ser Asn Ile Glu Thr Val Ile Glu Phe Gln Gln Lys Asn Asn
                165                 170                 175

Arg Leu Leu Glu Ile Thr Arg Glu Phe Ser Val Asn Ala Gly Val Thr
```

```
            180                 185                 190

Thr Pro Val Ser Thr Tyr Met Leu Thr Asn Ser Glu Leu Leu Ser Leu
        195                 200                 205

Ile Asn Asp Met Pro Ile Thr Asn Asp Gln Lys Lys Leu Met Ser Asn
    210                 215                 220

Asn Val Gln Ile Val Arg Gln Gln Ser Tyr Ser Ile Met Cys Ile Ile
225                 230                 235                 240

Lys Glu Glu Val Leu Ala Tyr Val Val Gln Leu Pro Leu Tyr Gly Val
                245                 250                 255

Ile Asp Thr Pro Cys Trp Lys Leu His Thr Ser Pro Leu Cys Thr Thr
            260                 265                 270

Asn Thr Lys Glu Gly Ser Asn Ile Cys Leu Thr Arg Thr Asp Arg Gly
        275                 280                 285

Trp Tyr Cys Asp Asn Ala Gly Ser Val Ser Phe Phe Pro Gln Ala Glu
    290                 295                 300

Thr Cys Lys Val Gln Ser Asn Arg Val Phe Cys Asp Thr Met Asn Ser
305                 310                 315                 320

Leu Thr Leu Pro Ser Glu Val Asn Leu Cys Asn Val Asp Ile Phe Asn
                325                 330                 335

Pro Lys Tyr Asp Cys Lys Ile Met Thr Ser Lys Thr Asp Val Ser Ser
            340                 345                 350

Ser Val Ile Thr Ser Leu Gly Ala Ile Val Ser Cys Tyr Gly Lys Thr
        355                 360                 365

Lys Cys Thr Ala Ser Asn Lys Asn Arg Gly Ile Ile Lys Thr Phe Ser
    370                 375                 380

Asn Gly Cys Asp Tyr Val Ser Asn Lys Gly Val Asp Thr Val Ser Val
385                 390                 395                 400

Gly Asn Thr Leu Tyr Tyr Val Asn Lys Gln Glu Gly Lys Ser Leu Tyr
                405                 410                 415

Val Lys Gly Glu Pro Ile Ile Asn Phe Tyr Asp Pro Leu Val Phe Pro
            420                 425                 430

Ser Asp Glu Phe Asp Ala Ser Ile Ser Gln Val Asn Glu Lys Ile Asn
        435                 440                 445

Gln Ser Leu Ala Phe Ile Arg Lys Ser Asp Glu Leu Leu
    450                 455                 460


<210> SEQ ID NO 17
<211> LENGTH: 568
<212> TYPE: PRT
<213> ORGANISM: Artificial Sequence
<220> FEATURE:
<223> OTHER INFORMATION: prefusion-stabilized RSV F protein (figure 11c)

<400> SEQUENCE: 17

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
```

-continued

```
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510
```

```
Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 18
<211> LENGTH: 574
<212> TYPE: PRT
<213> ORGANISM: Artificial Sequence
<220> FEATURE:
<223> OTHER INFORMATION: RSV A F consensus sequence

<400> SEQUENCE: 18

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300
```

-continued

```
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
        515                 520                 525

Thr Ile Ile Ile Val Ile Ile Val Ile Leu Leu Leu Leu Ile Ala Val
    530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 19
<211> LENGTH: 574
<212> TYPE: PRT
<213> ORGANISM: Artificial Sequence
<220> FEATURE:
<223> OTHER INFORMATION: RSV B F consensus sequence

<400> SEQUENCE: 19

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510
```

-continued

```
Leu His Asn Val Asn Thr Gly Lys Ser Thr Thr Asn Ile Met Ile Thr
        515                 520                 525

Ala Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```